(12) United States Patent
Barcaccia et al.

(10) Patent No.: US 9,732,391 B2
(45) Date of Patent: Aug. 15, 2017

(54) CICHORIUM SPP. MALE STERILE MUTANTS

(71) Applicant: T&T S.r.l. AGRICOLA, Chioggia, Venezia (IT)

(72) Inventors: Gianni Barcaccia, Legnaro (IT); Silvano Caenazzo Tiozzo, Chioggia (IT)

(73) Assignee: T&T S.R.L. AGRICOLA, Chioggia, Venice (IT)

( * ) Notice: Subject to any disclaimer, the term of this patent is extended or adjusted under 35 U.S.C. 154(b) by 479 days.

(21) Appl. No.: 14/091,051

(22) Filed: Nov. 26, 2013

(65) Prior Publication Data
US 2014/0157448 A1    Jun. 5, 2014

Related U.S. Application Data

(63) Continuation-in-part of application No. PCT/EP2011/058765, filed on May 27, 2011.

(51) Int. Cl.
*A01H 1/02* (2006.01)
*A01H 1/04* (2006.01)
*C12Q 1/68* (2006.01)
*A01H 5/02* (2006.01)
*C12N 15/82* (2006.01)

(52) U.S. Cl.
CPC ............. *C12Q 1/6895* (2013.01); *A01H 1/04* (2013.01); *A01H 5/025* (2013.01); *C12N 15/8289* (2013.01)

(58) Field of Classification Search
None
See application file for complete search history.

(56) References Cited

FOREIGN PATENT DOCUMENTS

FR        2832290 A1    5/2003
NL        FR 2832290 A1 *  5/2003  ............... A01H 1/02
WO        WO 9745548    12/1997

OTHER PUBLICATIONS

Gonthier et al, Theor Appl Genet (2013) 126:2103-2121.*
Cadelen et al, A consensus genetic map for chicory in Clabaut, Phd thesis, 2009, Universite Lillie, Sciences et Technologies.*
Ambrosi, et al., DNA Markers and FCSS Analyses Shed Light on the Genetic Diversity and Reproductive Strategy of Jatropha curcas L., Diversity May 2010, pp. 810-836.
Barcaccia, et al., Inheritance and mapping of 2n-egg production in diploid alfalfa, NRC May 2000, Genome 43, pp. 528-537.
Barcaccia, et al., Genomic DNA fingerprints as a tool for identifying cultivated types of radicchio (*Cichorium intybus* L.) from Veneto, Italy, Plant Breeding, Blackwell Verlag, 2003, pp. 178-183.
Cadalen, et al., Development of SSR markers and construction of a consensus genetic map for chicory (*Cichorium intybus* L.), Molecular Breeding, Jan. 2010, vol. 25, No. 4, pp. 700-722.
Denis, et al., Expression of Engineered Nuclear Male Sterility in Brassica napus, Genetics, Morphology, Cytology, and Sensitivity to Temperature, Plant Physiol, 1993, pp. 1295-1304.
Dubreucq, et al., Analyses of mitochondrial DNA structure and expression in three cytoplasmic male-sterile chicories originating from somatic hybridisation between fertile chicory and CMS sunflower protoplasts, Theoretical and Applied Genetics, Springer-Verlang, Apr. 1999, pp. 1094-1105.
Gonthier, et al., High-density genetic maps for loci involved in nuclear male sterility (NMS1) and sporophytic self-incompatibility (S-locus) in chicory (*Cichorium intybus* L., Asteraceae), Theoretical and Applied Genetics, Springer-Verlang, May 2013, pp. 2103-2121.
Hayden, et al., Application of multiplex-ready PCR for fluorescence-based SSR genotyping in barley and wheat, Springer Science and Business Media B.V., Mol Breeding, 2008, pp. 271-281.
Horn et al., A mitochondrial 16 kDa protein is associated with cytoplasmic male sterility in sunflower, Plant Molecular Biology, Feb. 1991, pp. 29-36.
Lucchin, et al., Handbook of Plant Breeding, Chapter 1, Vegetables, Spring Science and Business Media, LLC, 2008, pp. 1-46.
Mariani, et al., Induction of male sterility in plants by a chimaeric ribonuclease gene, Nature, Oct. 1990, vol. 347, pp. 737-741.
Moneger, et al., Nuclear restoration of cytoplasmic male sterility in sunflower is associated with the tissue-specific regulation of a novel mitochondrial gene, The EMBO Journal, 1994, vol. 13, No. 1, pp. 8-17.
Rambaud et al., Male-sterile chicory cybrids obtained by intergeneric protoplast fusion, Theoretical and Applied Genetics, Springer-Verlang, Mar. 1993, pp. 347-352.
Rambaud et al., Molecular analysis of the fourth progeny of plants derived from a cytoplasmic male sterile chicory cyhrid, Plant Breeding, Blackwell Wissenschafts-Verlag Apr. 1997, pp. 481-486.
VOS, et al., AFLP: a new technique for DNA fingerprinting, Oxford University Press, Nucleic Acids Research, Oct. 1995, vol. 23, No. 21, pp. 4407-4414.
Zhang, et al., Characterization and mapping of a male-sterility mutant, tapetum desquamation (t), in rice, Genome, Feb. 2008, pp. 368-374.
Varotto, et al., Production of asymmetric somatic hybrid plants between *Cichorium intybus* L. and *Helianthus annuus* L., Theoretical and Applied Genetics, Springer-Verlang, Aug. 2000, pp. 950-956.
Desprez, et al., Genetics and Breeding of Industrial Chicory, Academy of Agriculture, Paris France, Jan. 1994, vol. 80, No. 7, pp. 47-62.

(Continued)

*Primary Examiner* — David T Fox
(74) *Attorney, Agent, or Firm* — Tutunjian & Bitetto, P.C.

(57) ABSTRACT

The present invention relates to leaf chicory (*Cichorium intybus* subsp. *intybus* var. *foliosum*) nuclear recessive male sterile mutants, to a newly identified polymorphic molecular marker for the nuclear recessive male sterile character in this species, to methods for the selection of leaf chicory nuclear recessive male sterile mutants, to methods for the production of seed parent male sterile and pollen donor male fertile inbred lines of leaf chicory, including all cultivated types of radicchio, that are, respectively, homozygous for the nuclear recessive male sterile mutant allele or homozygous for the male fertile wildtype allele, and to methods for the constitution of F1 hybrids that are all heterozygous at the ms locus.

3 Claims, 8 Drawing Sheets

(56) References Cited

OTHER PUBLICATIONS

Gonthier, et al., Construction and characterization of two BAC libraries representing a deep-coverage of the genome of chicory (*Cichorium intybus* L., Asteraceae), BMC Research Notes, Aug. 2010, vol. 3, No. 1, pp. 1-10.

De Simone, et al., A first linkage map of *Cichorium intybus* L. using a one-way pseudo-testcross and PCR-derived markers, Molecular Breeding: New Strategies in Plant Improvement, Dec. 1997, vol. 3, No. 6, pp. 415-425.

Van Stallen, et al., Identification of commercial chicory cultivators for hydroponic forcing and their phenetic relationships revealed by random amplified polymorphic DNAs and amplified fragment length ploymorphisms, Plant Breeding, Jun. 2000, vol. 119, No. 3, pp. 265-270.

Quillet, et al., Cloning ans characterization of nuclear male sterility 1 (nms1) in chicory (*Cichorium intybus* L. Asteraceae), Eucarpia, Leafy Vegetables, Aug. 2011, pp. 1-14 and 73.

International Search Report dated Feb. 29, 2012 for International Application No. PCT/EP2011/058765.

J.W. Van Ooijen, JoinMap® 3.0 : Software for the calculation of genetic linkage maps, Wageningen, Oct. 2001.

D.D. Kosambi, The Estimation of Map Distances From Recombination Values, Annals Eugenics, 12: 172-175 (1944).

Arlette Reynaerts et al., Engineered genes for fertility control and their application in hybrid seed production, Scientia Horticulturae, 55 (Aug. 1993) 125-139.

* cited by examiner

CICHORIUM SPP. MALE STERILE MUTANTS

CROSS-REFERENCE TO RELATED APPLICATIONS

This application is a continuation-in-part of International Application No. PCT/EP2011/058765 filed May 27, 2011, the disclosure of which is incorporated herein by reference.

SEQUENCE LISTING

The instant application contains a Sequence Listing which has been submitted electronically in ASCII format and is hereby incorporated by reference in its entirety. Said ASCII copy, created on Dec. 18, 2013, is named 374-189(CIP)_SL.txt and is 4,201 bytes in size.

BACKGROUND

Technical Field

The present invention relates to *Cichorium* spp. nuclear recessive male sterile mutants of *Cichorium intybus* subsp. *intybus* var. *foliosum* (also known as leaf chicory), to newly identified polymorphic molecular markers tightly linked to the nuclear recessive gene that control the expression of the male sterile trait in leaf chicory, to methods for the selection of nuclear recessive male sterile mutants in leaf chicory, to methods for the production of inbred lines of leaf chicory showing male sterility (i.e. seed parent) and male fertility (i.e. pollen parent) of leaf chicory, including all cultivated types of Radicchio, and to F1 hybrids that are heterozygous at the locus for male sterility, being so characterized by male fertility.

Description of Related Art

In plant breeding the conventional methods for hybridizing and selecting plants on the basis of the observed phenotype are nowadays not the only methods used by plant breeders. Up to date, molecular genetics and biotechnology are widely used to produce transgenic plants, to produce new mutants and also within breeding programs wherein molecular markers can be essential tools for the selection of the characters of interest. In particular, when new characters of commercial and technical interest are created and/or discovered, a molecular marker for the tracking thereof is extremely useful and can be also the only way for the breeder for early selecting the plants carrying a number of desired characters of interest.

Although part of the steps of breeding programs normally include essentially biological processes such as controlled mating, the resort to technology becomes more and more essential at the initial stages of the breeding programs in order to obtain an early genetic selection of the desired plant phenotypes. In fact, nowadays, crop plants are selected for a high number of desired traits, the selection often being based on pyramiding the superior alleles for several genes. It follows that, at each generation, the genetic recombination through the independent assortment of the genes causes a wide random redistribution of all the alleles including the ones coding for the characters of agronomic and commercial interest. For this reason breeding programs avail themselves more and more frequently of molecular genetics techniques that allow the breeders to carry out a precise selection and/or production of plants expressing the desired characters (corresponding to specific genotypes that combine superior alleles for a number of genes), the techniques being particularly efficient when molecular markers linked to the loci of the genes of interest, said markers being polymorphic and allowing the tracking of the alleles and traits of interest.

Molecular markers with co-dominant inheritance patterns (i.e., capacity to distinguish the heterozygous locus for the two homozygous ones for a given gene or genome sequence), such as microsatellite markers, are of particular interest in order to allow a correct selection of the specific alleles and genotypes desired. A tight linkage of the marker to the locus of interest will result in the co-segregation of a specific allele of the marker with a specific allele of the gene mapping in said locus, thus allowing a very refined tracking of the desired allele/s at that locus. It is therefore essential to identify reliable molecular markers for characters that may be desirable, in particular when the characters of interest are genetically recessive.

In crop plants, commercial F1 hybrids are populations of plants of high commercial interest manifesting extreme vigour, being highly heterozygous (for most of the genes or at least heterozygous for the genes of interest). More precisely, for F1 hybrid plants the term "heterosis" is used, where this term officially indicates in genetics the greater vigour in terms of size, growth rate, resistance to biotic and abiotic stresses, and fertility and productivity of hybrids compared to their parental plants, usually stemmed from controlled crosses between highly inbred lines, which are homozygous for different alleles at each locus being considered. Consequently, heterosis is always associated with increased heterozygosity. These plants are known to produce an F2 progeny (and F3, F4, etc in the following generations) of much lower quality with respect to the F1 generation because of genetic segregation and recombination mechanisms.

The loss of the traits of commercial interest in the generations after F1 is due to the high number of genes of interest for which the F1 plant is heterozygous and to the genetic recombination by means of independent assortment thereof, assortment that will randomly spread the alleles of the genes of interest thus providing F1+n (n≥1) genotypes that are not anymore carrying the desired genotype (and the resulting vigorous phenotype) of F1 in all the loci of interest. It is hence essential, in breeding programs, to be able of tracking the genes of interest, of discriminating between the desired and the undesired alleles thereof, and of generating two antagonist parental lines that are homozygous for different alleles of the same genes of interest that when crossed one with the other will provide, at each hybridization between said parental plants, the desired F1 hybrid. In other words, the crucial part of a breeding program aimed at the constitution of F1 hybrids deals with an accurate genetic selection of the parental plants that is effectively carried out with the aid of molecular genetics techniques.

For the best results in producing F1 hybrids of commercial value, the seed producer parental line (also called "seed parent") is preferably male sterile thus avoiding completely the occurrence of self-pollination and presence in the F1 generation of inbred progeny seeds in disadvantage to the production of F1 hybrids. For this reason, in absence of an efficient genetic male sterility system, when stamens and pistils occur in the same flower of a fully male fertile seed parent, the plant is normally made male sterile by physical removal of the anthers from the flowers before pollen dispersal.

It is obvious that the introduction or identification of male sterility genes, i.e. genes responsible for the fertility of the male part of the flower that, upon mutation, can provide a male sterile plant would be preferable. Male sterile mutants, that cannot produce viable pollen grains or functional anthers, allow the exploitation of heterosis in F1 hybrid populations of many agricultural and horticultural crops are hence highly desirable.

Two kinds of male sterility can be observed in plants: nuclear and cytoplasmic male sterility. The former type of genetic male sterility is based solely on recessive mutations that affect different functions in nuclear genes (ms indicates the recessive allele causing male sterility whereas Ms indicates the wild type dominant allele rendering the plant male fertile), while cytoplasmic male sterility (CMS) is maternally inherited and mainly due to mutations in the expression of mitochondrial genes that are inherited only maternally by the egg cell cytoplasm. Moreover, in genotypes showing CMS, male fertility can be eventually restored by nuclear-encoded fertility restorer (Rf) genes. In several species, nuclear and/or cytoplasmic male-sterility has been used to produce female parental lines and exploited for the production of hybrid seeds through controlled pollination with male parental lines showing specific combining ability.

Cultivated chicory (*Cichorium intybus* subsp. *intybus* L.) is a diploid plant species (2n=18), belonging to the Asteraceae family, subfamily Cichoriodeae, tribe Lactuceae or Cichorieae. These species are naturally allogamous, due to an efficient sporophytic self-incompatibility system. In addition, outcrossing is promoted by a floral morpho-phenology (i.e., proterandry, having the anthers mature before the pistils) unfavourable to selfing in the absence of pollen donors and by a favourable competition of allo-pollen grains and tubes (i.e., pollen genetically diverse from that produced by the seed parents, usually called auto-pollen). Long appreciated as medical plants by ancient Greeks and the Romans, leaf chicory varieties are nowadays amongst the most important cultivated vegetable crops, being used mainly as component for fresh salads or more rarely cooked according to local traditions and alimentary habits. At present, this species are grown all over continental Europe, in South Western Asia, and on limited areas in Northern America, South Africa, and Australia.

Two main groups can be recognized within *C. intybus* subsp. *intybus* to which all the cultivated types of chicory belong: the first, which refers to the var. *foliosum*, traditionally includes all the cultivar groups whose commercial products are the leaves (i.e. leaf chicory), while the second regards the var. *sativum* and comprises all the types whose commercial product, either destined to industrial transformation or direct human consumption, is the root (i.e. root chicory) (for the taxonomic classification of *Cichorium intybus* botanical varieties, see Lucchin M., Varotto S., Barcaccia G. and Parrini P. (2008). Chicory and Endive. In: Handbook of Plant Breeding, Vegetables I: Asteraceae, Brassicaceae, Chenopodicaceae. Edited by Jaime Prohens-Tomás and Fernando Nuez. Springer Science, New York, USA. pp. 1-46). The cultivar groups of leaf chicory include mainly Witloof chicory, Pain de sucre, Catalogne and Radicchio. In particular, "Radicchio" is the Italian common name that has been adopted by all the most internationally used languages to indicate a very differentiated group of chicories, with red or variegated leaves, traditionally cultivated in North Eastern Italy. All the red types of Radicchio now being cultivated seem to derive from red-leaved individuals firstly introduced in XV century. According to historical information (Bianchedi A. (1961) I radicchi di Treviso. L'Italia Agricola. 1: 37-51), the cultivation of red chicory goes back to the first half of XVI century. For sure, the original type has to be identified with the "Rosso di Treviso" which has been for long the only cultivated Radicchio in the Venetian territories. Originally selected around 1930, nowadays "Rosso di Chioggia" is by far the most widely grown among the various types of Radicchio and the one which presents the highest within-type differentiation as far as the availability of cultivars able to guarantee an almost complete year round production. As a matter of fact, it has shown a great adaptability to very different environmental situations all around the world, becoming the most grown type of Radicchio outside the Italian country and the most known at international level (Lucchin et al., 2008).

It is worth mentioning that traditionally cultivated populations of leaf chicory, in general, and radicchio, in particular, were developed by mass selection in order to obtain uniform populations characterized by valuable production and acceptable commercial head size and shape. Newly released varieties are mainly synthetics produced by intercrossing a number of phenotypically superior plants, selected on the basis of morpho-phenological and commercial traits. More rarely, plants are also evaluated genotypically by means of progeny tests. Synthetics have a rather large genetic base and are represented by a heterogeneous mixture of highly heterozygous genotypes sharing a common gene pool. In recent years, methods for the constitution of F1 hybrids have been developed by private breeders and seed firms. Details on the procedure for the constitution of such hybrids are not available in the current literature and it may be presumed that each company has developed its own protocol, mainly in accordance to the genetic material it has at disposal and to the possibility of applying a more or less efficient control on the F1 hybrid seed production phase.

As a matter of fact, the strong self-incompatibility system, which hinders obtaining highly homozygous parents, and the absence of a male-sterility factor within the species or in sexually compatible species, made it generally difficult to propose an efficient F1 seed production scheme and, most of all, to consider these newly commercial populations or varieties as true F1 hybrids for leaf chicory.

As it happens for most allogamous species, in leaf chicory detectable heterosis effects are present and hybridization between genotypes selected on the basis of their specific combining ability gives vigorous and uniform progenies. Consequently, the constitution of F1 hybrid populations is profitable in a practical breeding scheme and it is also feasible on a large commercial scale by the selection of self-compatible genotypes, for the production of inbred lines, and the identification of genotypes showing male-sterility, to be used as see parents for the hybridization with pollen donors. It is therefore expected that F1 hybrid populations will be bred and adopted with increasing frequency for leaf chicory. This is particularly true for the cultivated types that take a great advantage from the uniformity of the marketed products, as this is often the key for the customer's appreciation.

Notwithstanding the high commercial interest, the presence of a naturally occurring CMS system has not been reported in leaf chicory whereas strategies to genetically engineering male sterility were used in Magdeburg, Witloof and Chioggia genotypes (reviewed in Lucchin M., Varotto S., Barcaccia G. and Parrini P. (2008). Chicory and Endive. In: Handbook of Plant Breeding, Vegetables I: Asteraceae, Brassicaceae, Chenopodicaceae. Edited by Jaime Prohens-Tomas and Fernando Nuez. Springer Science, New York, USA. pp. 1-46).

In a first approach, transgenic male sterile lines of leaf chicory were produced by expressing the ribonuclease gene RNase from *Bacillus amyloliquefaciens* (known as BARNASE) under the control of a tapetum-specific promoter originally isolated from tobacco (TA-29) (see Mariani C., De Beuckeleer M., Trueltner J., Leemans J and Goldberg R. B. (1990). Induction of male sterility in plants by a chimaeric ribonuclease gene. Nature, 347: 737-741). Restorer lines for these male-sterile lines were obtained by expressing the gene coding for the so-called BARSTAR, the intracellular inhibitor of BARNASE under control of the same promoter (Denis M., Delourne R., Gourret J. P., Mariani C. and Renerd M. (1993). Expression of engineered nuclear male sterility in Brassica napus: genetics, morphology and sensitivity to temperature. Plant Phys., 101(4): 1295-1304; Reynaerts A., Van de Wiele H., de Sutter G. and Janssens J. (1993). Engineered genes for fertility control and their application in hybrid seed production. Sci. Hort., 55: 125-139). The development of inbred lines and male-sterile lines provided a reliable pollination control and allowed a new hybrid seed production system, which has been registered as SeedLink™. This system for genetically engineering pollination in plants was invented and implemented by the private industry Plant Genetic Systems (Belgium).

Somatic hybridization by means of protoplast symmetric fusion between chicory and the CMS line of sunflower PET-1 was also attempted in order to promote the regeneration of interspecific hybrid plants. This kind of CMS in sunflower was identified in an interspecific cross between Helianthus petiolaris and Helianthus annuus, and it was associated with the expression of the mitochondrial gene ORF522, encoding a 15-kD polypeptide. The ORF522 gene was originated by a recombination event at the 3' of atp1 gene and its protein is detectable in flowers of CMS but not of restored lines (Horn R., Köhler R. H. and Zetsche K. (1991). A mitochondrial 16-kDA protein is associated with cytoplasmic male sterility in sunflower. Plant Mol. Biol., 17: 29-36; Monegèr F. and Smart C. J. (1994). Nuclear restoration of cytoplasmic male sterility in sunflower is associated with the tissue-specific regulation of a novel mitochondrial gene. EMBO J., 13(1): 8-17). The hybrid plants obtained after somatic symmetric fusion were cytoplasmic hybrids, cybrids, and showed mtDNA rearrangements, indicating that symmetric fusion had the tendency to maintain the chicory mitochondrial genome. Three different kinds of sterility were observed: i) plant with anthers lacking dehiscence without, or with non-viable, pollen; ii) complete absence of the anthers; and iii) absence of both anthers and styles or the presence of reduced styles. One of these male-sterile plants was used for the production of F1 hybrids whose yields were equal to or higher that those of traditional varieties (Rambaud C., Dubois J. and Vasseur J. (1993). Male-sterile chicory cybrids obtained by intergeneric protoplast fusion. Theor. Appl. Genet., 87: 347-352; Rambaud C., Bellamy A. Dubreucq A., Bourquin J-C. and Vasseur J. (1997). Molecular analysis of the fourth progeny of plants derived from cytoplasmic male sterile chicory cybrid. Plant Breed., 116: 481-486).

In a subsequent work, three different CMS chicory cybrids were backcrossed to Witloof chicory in order to transfer the male sterile cytoplasm from an industrial chicory to a Witloof genetic background. The transcript analysis revealed that the ORF522 is weakly expressed or not expressed at all in the cybrids. This finding led Dubreucq et al. (1999) to conclude that ORF522 cannot be associated to the CMS observed in the chicory cybrids and to suggest that they presented a novel form of CMS, different from that of sunflower. Protoplast asymmetric fusion was used to produce male sterile somatic hybrids between a Rosso di Chioggia genotype and a PET-1 sunflower CMS line. At anthesis the regenerated cybrids had fewer and non-viable pollen grains but they could set seeds when free-pollination occurred (Varotto S., Nenz E., Lucchin M. and Parrini P. (2001). Production of asymmetric somatic hybrid plants between Cichorium intybus and Helianthus annuus. Theor. Appl. Genet., 102: 950-956). Overall results collected so far using interspecific protoplast fusion experiments suggest that male-sterile cybrid plants can be actually regenerated in chicory. Nevertheless, it appears that mitochondrial genome re-arrangements lead to the creation of novel CMS chicory types instead of transferring the desired trait from CMS sunflower lines. The methods of transgenesis useful for making cytoplasmic male sterile chicory plants comprising the ORF 522 of Helianthus annuus was patented by Delesalle et al. (2004, see U.S. Pat. No. 6,803,497). As a matter of fact, the development of inbred lines and male-sterile lines based on this biotechnological approach failed to provide any reliable hybrid seed production system in chicory.

No endogenous recessive nuclear gene providing upon mutation a male sterile phenotype has so far been identified in leaf chicory (Cichorium intybus subsp. intybus var. foliosum), while a male sterile mutant having a not well-defined genetic inheritance has been reported for root chicory (Cichorium intybus subsp. intybus var. sativum). The latter mutant, apparently characterized by functional male sterility although not cytologically documented by Desprez et al. (Desprez B. F., Delesalle L., Dhellemmes C. and Desprez M. F. (1994) Génétique et amélioration de la chicorée industrielle. CR Acad. Agr. Fr. 80(7): 47-62) has been patented in the République Française on 1 Feb. 2002 by NUNHEMS ZADEN BV (Stérilité male de legumes de Cichorium cultivé et utilisation pour la production de semences hybrides, see No de publication: FR2832290). Recently, the use of high-density molecular maps allowed the fine mapping of molecular markers linked to the genomic locus involved in nuclear male sterility (termed NMS1): in particular, the gene responsible for male sterility trait in root chicory was found associated to the linkage group 5 of Cichorium intybus L. (Gonthier L., Blassiau C., Mörchen M., Cadalen T., Poiret M., Hendriks T., Quillet M. C. (2013) High-density genetic maps for loci involved in nuclear male sterility (NMS1) and sporophytic self-incompatibility (S-locus) in chicory (Cichorium intybus L., Asteraceae). Theoretical and Applied Genetics, 126(8): 2103-2021. doi: 10.1007/s00122-013-2122-9).

Concerning markers, only a few genetic studies using molecular markers have been carried out on Cichorium spp. mainly to characterize commercial varieties and experimental materials, to evaluate the genetic homogeneity and purity, respectively, of inbreds and hybrids, and to investigate phylogenetic relationships between cultivars and cultivar groups of C. intybus and other species, both cultivated and wild, belonging to the same genus. Amplified fragment length polymorphism (AFLP) and random amplified polymorphic DNA (RAPD) markers were also used to construct the first genetic map of C. intybus. More recently, a new genetic map was constructed for chicory using simple sequence repeat (SSR or microsatellite) markers by Cadalen et al. (Cadalen T., Mörchen M., Blassiau C., Clabaut A., Scheer I., Hilbert J-L., Hendriks T. and Quillet M-C. (2010). Development of SSR markers and construction of a consensus genetic map for chicory (Cichorium intybus L.). Molecular Breeding, 25: 699-722). This consensus genetic map, which includes 9 homologous linkage groups one for each of the 9 haploid chromosome complements, was obtained after the integration and ordination of molecular marker data of one witloof chicory and two industrial chicory progenies.

It is worth emphasizing that molecular markers in *Cichorium* spp. have been exploited for selecting the mother plants of synthetics as well as for determining the distinctiveness, uniformity and stability, i.e. DUS testing, of newly bred varieties. In *Cichorium* spp., molecular markers should also find utility for assessing the genetic homogeneity and homozygosity of inbred lines produced by repeated selfing, measuring the genetic diversity among inbred lines in order to plan crosses and maximize heterosis in the experimental F1 hybrids, and evaluating the genetic purity and heterozygosity of seed stocks of commercial F1 hybrids.

In conclusion, providing male-sterility in the leaf chicory species will open new frontiers for breeding new varieties in general, especially if this trait can be profitably transferred to elite lines and precociously identified by molecular diagnostic assays suitable to perform marker-assisted selection programs.

SUMMARY

The present invention discloses male sterile mutants of leaf chicory (*Cichorium intybus* subsp. *intybus* var. *foliosum*), induced and developed by the inventors, wherein the new ms trait is inherited as a single recessive nuclear gene (herein denominated generally ms or Cims-1 as opposite to the Ms wild type dominant gene) character.

The invention discloses also a new polymorphic genetic microsatellite marker tightly linked to the locus where the Ms gene is located. This marker allows to track the mutant allele ms conferring the male-sterility trait of the invention in subsequent selfing and crossing procedures, and to make sure that this trait is advantageously inherited in highly inbred plants in the breeding program suitable for the selection of seed parent lines.

In fact, the identification of a molecular polymorphic marker tightly linked to the locus where the Ms gene is located allows the identification of a ms-linked genotype of the marker and the tracking of the ms gene (also in heterozygous loci) upon generation of a msms seed parent that can conveniently be homozygous also for several other genes of interest. Hence, the marker is suitable for use in methods for the generation of msms seed parent plants and in methods for the generation of Msms F1 commercial hybrids, wherein the detection of the marker alleles linked to the ms mutation allows following the trait during all the steps of the process.

The mutants of the invention have been developed by the inventors and have been described for the first time at either the cytological and genetic levels, since the analysis of the mutation induced by the inventors has demonstrated that the mutation itself affect a single nuclear gene providing a recessive trait causing male sterility when homozygous (msms). Moreover, the inventors have documented that the mutation leads the microspores of each tetrad to arrest their development at the uninucleate stage, degenerating before their release from the tetrads. At full flowering, in genotypes msms all the microspores of dehiscent anthers were found shapeless, shrunken and much smaller than wild-type ones. The inventors have demonstrated that pollen grains are never produced in mature anthers, demonstrating a full expressivity of the trait with mutants being 100% male sterile.

The invention hence provides for the first time male sterile mutants of leaf chicory, a molecular marker tightly linked to the ms gene, methods for the identification of mutants in this species carrying the ms mutation at the homozygous or heterozygous state, methods for the production of homozygous msms or heterozygous Msms plants of leaf chicory, parts thereof or derivatives thereof, methods for the production of msms seed parent plants, and methods for the production of heterozygous Msms F1 hybrids of leaf chicory.

The invention also provides a diagnostic assay for the early screening in leaf chicory populations of the ms mutation herein provided by using the identified polymorphic marker and plant genotypes carrying the ms mutation of the invention.

DETAILED DESCRIPTION OF THE SEQUENCES

Figure 1:
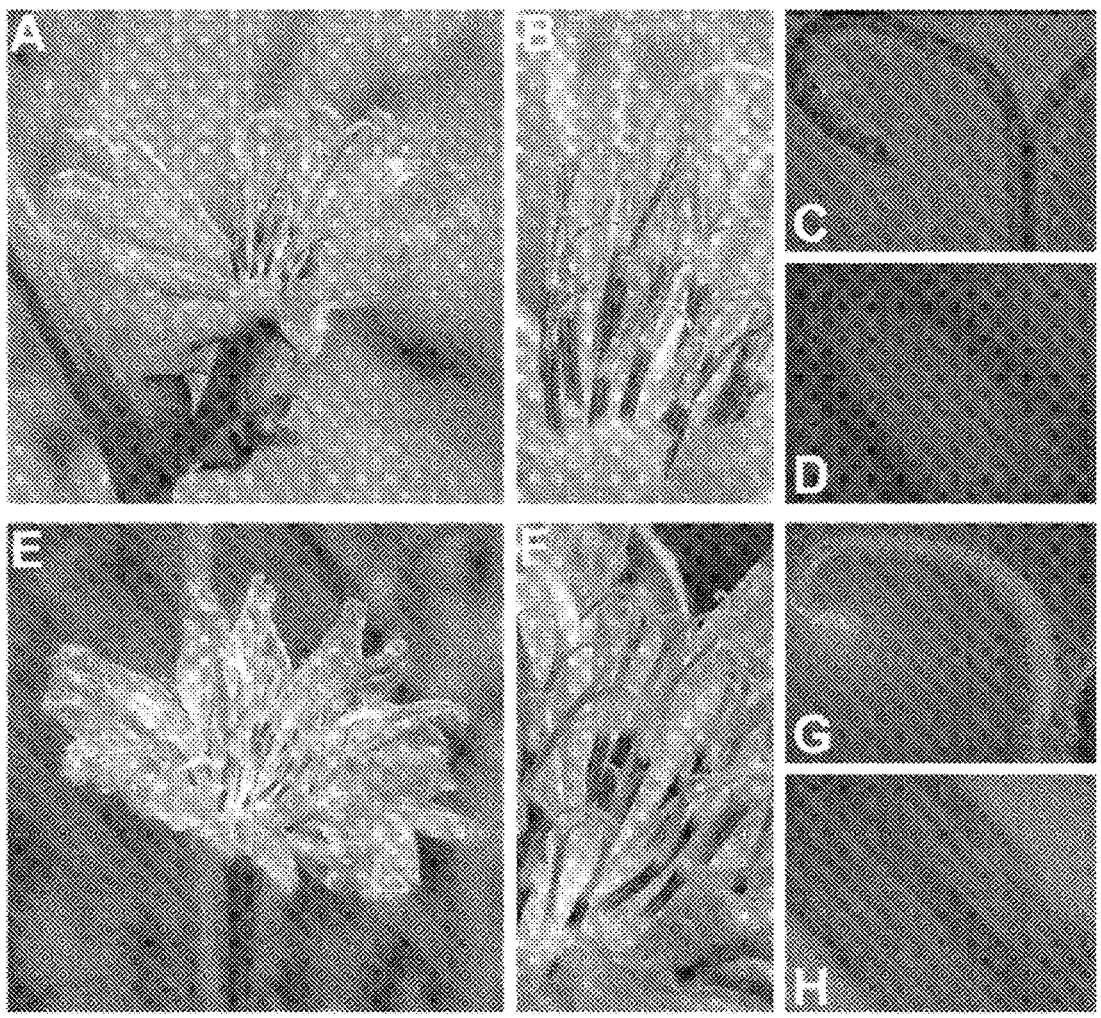
FIG. 1: Phenotype of wild-type plants (A-D) and male-sterile mutants (E-H) of red chicory (*Cichorium intybus* L.). Details of macroscopic (A, B) and microscopic (C, D) features are given for the wild-type anthers in parallel with mutant anthers (E, F and G, H, respectively).

```
                                           SEQ ID NO 1
TGAGTGATTCTCGGAGAGTT(TC)CAGAGATCATTGCTTGTGTA
```

DNA marker sequence linked to ms mutation in *Cichorium* spp. containing a variable number of thymine-cytosine repeats variable (TC)n

```
                                           SEQ ID NO 2
CTTGGAGGTGTGAGTGATTCTCGGAGAGTT(TC)CAGAGATCATTGCTT

GTGTAATTCTCGCTGATTTCAGTTCATTGTCGTCTCTCTTTGCTGTTTC

GTA
```

DNA marker sequence linked to ms mutation in *Cichorium* spp. containing a variable number of thymine-cytosine repeats (TC)n, with n ranging from 27 to 33 (SEQ ID NO:7) in the ms mutants, that start from nucleotide position 31 (the total length ranges from 141 to 163 nucleotides according to the leaf chicory genotype) (full-length sequence disclosed as SEQ ID NO:6).

```
forward primer for marker comprising or
consisting of SEQ ID 2 amplification
CTTGGAGGTGTGAGTGATTCT 21 (SEQ ID NO: 3)

reverse primer for marker comprising or
consisting of SEQ ID 2 amplification
TACGAAACAGCAAAGAGAGAC 21 (SEQ ID NO: 4)

SEQ ID NO 5
GCCATTCCTTTCAAGAGCAGATCTTAAAAGTCTAAAGGGTTTGTGAATT

GTGTGTGTGCGTGTGTGTGTGTGTAAATTATTATGGTCCTAAAATGGAT

GATATTTGTATTTAAGATCTCCATGCTTGTTTATCAACTCTCTTCTATG

ATATGAACAAATATTGTTGCGGTTTTGGGTT
```

DNA marker genetically linked to the ms locus in the linkage group 4 of *Cichorium intybus* including a variable number of thymine-guanine repeats (TG) with total length in the ms mutants equal to 178 nucleotides.

DETAILED DESCRIPTION OF PREFERRED EMBODIMENTS

The Male-Sterile Mutant of Radicchio (Leaf Chicory)

The present invention describes for the first time a male sterile leaf chicory (*Cichorium intybus* subsp. *intybus* var. *foliosum*) mutant, parts or elaborates thereof, wherein the male sterility trait is due to a nuclear recessive mutation (ms) linked to a polymorphic genetic marker comprising SEQ ID NO 1 or SEQ ID NO 2 or consisting of SEQ ID NO 2.

The mutant plants of the invention are plants of "Radicchio" belonging to the species *C. intybus* subsp. *intybus* var. *foliosum* to which refer all the cultivated types of leaf chicory. Among the cultivar groups, "Radicchio" is the Italian common name that has been adopted by all the most internationally used languages to indicate a very differentiated group of chicories, with red or variegated leaves.

By plant parts it is herein intended parts of the plant carrying nuclear genetic information, starting from the nucleus, cells, tissues, leaves, roots, stems, flowers, and the like whereas by elaborates it is herein intended processed parts of the plant as defined above (e.g. flour, powder, fragments, extracts etc.) wherein said nuclear genetic information is still detectable.

The invention also provides mutant leaf chicory plants or parts or elaborates thereof, wherein the mutation described above is in heterozygosity (genotype Msms such as F1 hybrids), hence directly detectable only with the marker of the invention. For indirect detection a number of controlled pollination by means of selfing or back-crossing should be carried out until the homozygous recessive (genotype msms such as in seed parent inbred lines) mutant phenotype is expressed in the segregating F2 or BC1 progeny.

Figure 2:
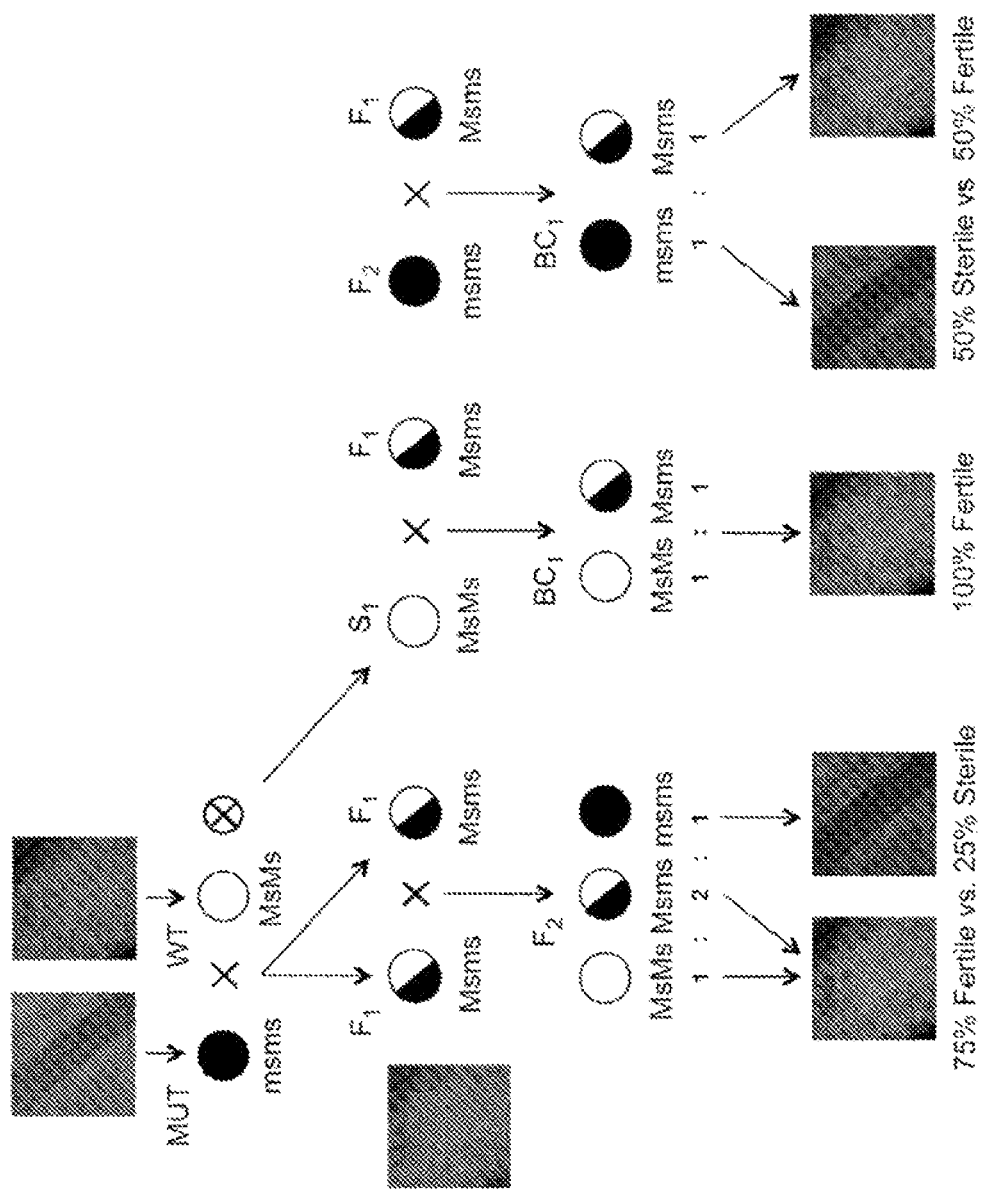
FIG. 2: Genetic analysis of male-sterile mutants based on segregation patterns observed in F2 and BC1 progenies. Each of the male sterile mutants was crossed as seed parent with a wild type pollinator belonging to the same subsp. Several F1 plants from each hybrid population were then selfed and crossed in pair-wise combinations in order to obtain segregating F2 progenies. Moreover, F1 plants were also backcrossed as pollen donors with either male sterile mutants belonging to F2 progenies or wild type plants of 51 progenies stemmed from selfing in order to obtain segregating BC1 progenies. These experimental populations were used to establish the inheritance pattern of the mutation and to map the male sterility gene.

In particular, when segregating progeny plants of the msms mutants are produced, said plants will be either homozygous or heterozygous at the locus for male fertility/sterility, depending on the type of cross-pollination performed to produce the progeny (cfr. FIG. 2), and will be detectable at early developmental stages by using the marker herein provided and by comparing the marker alleles of the progeny to the marker alleles of the msms mutant. The progeny carrying the mutation in heterozygous form will have one allele (ms) identical to that of the male sterile mutant for the marker of the invention, which will be inherited in the segregating generations.

In an embodiment of the invention the progeny heterozygous for the ms mutation is a F1 commercial hybrid. The invention in fact provides F1 hybrids that can be selected for several characters of interest, one of them being the heterozygosity for the ms mutation herein described.

The mutants of the invention have been characterized in great details for the developmental pathway of micro-sporogenesis and gametogenesis, and the inheritance pattern of the gene underlying the male-sterility trait. Moreover, the fine mapping of the mutant locus has also been accomplished by using molecular markers. Experimental results on the male sterile mutants are presented below in order to describe their phenotype "anthers with no pollen grains" and to discriminate their genotype on the basis of a based on the "polymorphic microsatellite sequence" described below. The potentials of the use of male sterile mutants for breeding new F1 hybrid populations are critically discussed, analyzing also the advantages in comparison to synthetic varieties traditionally constituted in leaf chicory, especially "Radicchio".

In alternate embodiments, a male sterile mutant of a plant, parts or derivatives thereof is provided, wherein the male sterility trait is controlled by a nuclear recessive mutation (ms). The nuclear recessive mutation (ms) may be ascribable to a single gene linked 5.8 cM apart to a polymorphic molecular marker locus finely mapped on linkage group 4 comprising a microsatellite or simple sequence repeat (TC)n in SEQ. ID NO 1 or 2 and the progeny thereof.

Progeny plants may show either a mutant or a wild-type cytological phenotype for said trait and may be at least heterozygous for said mutation at the ms locus.

In alternate embodiments, F1 hybrid plants or parts or elaborates thereof obtained using the plant(s), parts or derivatives thereof described herein are provided.

In alternate embodiments, segregant progeny plants or parts or elaborates thereof obtained using the F1 hybrid plants or parts or elaborates thereof described herein are provided.

The DNA Marker Linked to the Mutation Responsible for Male-Sterility

The ms mutations of the invention are recessive mutations of a putatively identified candidate but not yet characterised nuclear gene that the inventors have found to be tightly linked to a new polymorphic molecular marker coded comprising SEQ ID NO 1. In an embodiment, the marker comprises or consists of SEQ ID NO 2.

The marker of the invention comprises a Simple Sequence Repeat (SSR) i.e. a (TC)n repeat wherein n is an integer higher than 1 and the polymorphic alleles thereof differ in the number n of repeats of the TC dinucleotide within SEQ ID NO 1 or within SEQ ID NO 2.

In one embodiment of the invention n is comprised between 27 and 33, i.e. n can be 27, 28, 29, 30, 31, 32, 33 however, the number of repeats can vary from the ones indicated herein without changing the tight linkage of the marker to the locus where the ms trait maps hence alleles where n is different from the ones indicated above are encompassed by the present invention.

The marker is tightly genetically linked to the locus wherein the ms mutation maps and it is also associated to the linkage group 4 of the *Cichorium intybus* consensus map along with another Simple Sequence Repeat (SSR) i.e. a (TG)n repeat within SEQ ID NO 5.

Linkage is defined as the association between two or more genes such that the traits they control tend to be inherited together (i.e., the genes are transmitted together to the offspring unless they recombine through crossing-over events). More precisely, genes or sequences are genetically associated because they physically reside on the same chromosome. In this specific case, linkage is the association in inheritance of a Mendelian factor (i.e., the gene controlling male sterility/fertility) and a microsatellite marker (i.e., the DNA sequence corresponding to simple nucleotide repeats) so that the segregation pattern of the alleles at these two genomic loci is expected to deviate from independent assortment.

The closest the genes or sequences, the lowest the genetic recombination between them is observed as result of crossing-over events. Consequently, a linkage group is a group of genes or sequences having their loci on the same chromosome and a linkage map is a map of a given chromosome showing the relative positions of the known genes or sequences on that chromosome of a given species.

The relative distance between two loci is calculated on the basis of the frequency of recombinant (i.e. non-parental) phenotypes between said loci, which is directly calculated using the frequency of recombinant gametes (i.e. gametes that contain recombinant chromosomes). The frequency of recombination is given by the number of recombinants divided the total number of progeny individuals. This frequency is used as a guide in assessing the relative genetic distances between mapped loci on a linkage group.

In the present application, the marker comprising SEQ ID NO 1 or SEQ ID NO 2 (or consisting of SEQ ID NO 2), herein denominated also E02M09/99, is linked to the locus where the ms mutation maps, i.e. is at a certain distance from it, on the same chromosome. In other words, the locus of the ms mutation and the marker of the invention are part of the same linkage group. In particular, the marker shows a mean recombination frequency with the ms mutation locus (corresponding to the locus of the relative wt gene) of about 5.8%.

The mutant of the invention can also be defined as a male sterile leaf chicory mutant plants, parts or elaborates thereof, wherein the male sterility trait is due to a nuclear recessive mutation (ms) linked with a mean recombination frequency of about 5.8% to a polymorphic genetic marker comprising SEQ ID NO 1 or comprising or consisting of SEQ ID NO 2. The same applies to the mutant progeny heterozygous at the locus for the male sterility trait, Msms.

The mean recombination frequency observed, corresponds to a distance between the two loci, after correction with the Kosambi's function (that takes into account some possible interference) of about 6 cM. In genetics, a centimorgan (abbreviated cM), or map unit, is a unit of recombinant frequency for measuring genetic linkage. Two markers on a chromosome are 1 cM apart if they have a 1% chance of being separated from each other by a crossing-over in a single generation. The centimorgan is often used to infer distance along a chromosome. Assuming that 1 cM is equivalent to about 500 Kb, the distance between the marker comprising SEQ ID NO 1 and the locus for the ms mutation or the wt gene thereof, is of about 3000 Kb.

In fact, the Mendelian factor responsible for male-sterility herein described (i.e. the ms mutation and the wt corresponding gene) has been experimentally found by the inventors as tightly linked with the molecular marker E02M09/230. When the datasets for both the trait and the marker were analyzed together, there was a significant deviation in the segregation data from the expected 1:1:1:1 ratio. The genetic determinant for male-sterility was found tightly associated with the diagnostic marker, as their alleles were preferentially inherited together (Fisher's 2×2 contingency test: $\chi2=75.3$ with P<0.0001). However, recombination events were apparently possible in the chromosome block carrying the male-sterility gene. In fact, this gene was associated with the AFLP-derived marker E02M09/230 containing a perfect microsatellite motif (TC/GA)n, with n ranging from 27 to 33 (SEQ ID NO:7), that was converted into a SCAR marker with a total length varying up to 163 nucleotides (DNA marker E02M09/163). Genetic co-segregation analysis revealed that DNA marker E02M09/163 is located in a chromosome window spanning about 6 cM that belongs to linkage group 4 of the consensus genetic map of chicory (Cadalen T., Mörchen M., Blassiau C., Clabaut A., Scheer I., Hilbert J-L., Hendriks T. and Quillet M-C. (2010). Development of SSR markers and construction of a consensus genetic map for chicory (*Cichorium intybus* L.). Molecular Breeding, 25: 699-722) likely characterized by active crossing-over sites and densely saturated by expressed sequence tags. The mean recombination frequency between the male-sterility trait and the E02M09/163 molecular marker containing a polymorphic microsatellite repeat was equal to 5.8%. The assignment of the gene, whose mutation is responsible for male-sterility in Radicchio (leaf chicory), to the linkage group 4 of the consensus genetic map of *Cichorium intybus* was obtained by testing the co-segregation of mapped molecular markers with the mutant phenotype in F2 and BC1 experimental populations. In particular, we assayed a total of 9 specifically selected marker loci so to have one reference SSR marker for each of the nine linkage groups of *Cichorium intybus* (Cadalen T., Mörchen M., Blassiau C., Clabaut A., Scheer I., Hilbert J-L., Hendriks T. and Quillet M-C. (2010). Development of SSR markers and construction of a consensus genetic map for chicory (*Cichorium intybus* L.). Molecular Breeding, 25: 699-722). Among the SSR markers publicly available for the chicory genome, the marker locus coded as EU03H01 containing an imperfect microsatellite motif (TG/CA)nCG/CG(TG/CA)n, with total n varying up to 11 (SEQ ID NO:8) for a length corresponding to 178 nucleotides (DNA marker EU03H01/178), was found associated to the male-sterility trait. The mean recombination frequency with the EU03H01/178 molecular marker was around 12.2%.

It can therefore be established that the two DNA markers and the ms locus are genetically associated in the same linkage group (i.e. LG4), and that this linkage is such that a chromosome window characterized by a total recombination frequency of about 18% can be observed between the two marker loci. As a consequence, the two marker loci enclosing the ms gene are at a genetic distance of about 19 cM. In fact, after correction of the recombination frequency estimates with the Kosambi's mapping function, it can be stated that our E02M09/163 and EU03H01/178 markers are mapped about 6 cM and 13 cM apart from the ms locus, respectively. The probability that both markers genetically recombine from the ms locus because of the occurrence of a double crossing-over is therefore very low being less than 1%.

In an embodiment of the invention, the ms mutation underlying male-sterility of Radicchio (leaf chicory) plants will be genetically associated with a microsatellite DNA marker, including (TC/GA)n nucleotide repeats in SEQ ID NO 1 and/or in SEQ ID NO 2 with n varying in number from 27 or 33 (SEQ ID NO:7), that is physically positioned in the linkage group 4 of the *Cichorium intybus* genome consensus map. In addition, the ms mutation underlying male-sterility of Radicchio (leaf chicory) plants will be genetically associated also with another DNA marker, including a sequence that contains (TG/CA)nCG/CG(TG/CA)n nucleotide repeats reported in SEQ ID NO 5, that is genetically mapped in the linkage group 4 of the *Cichorium intybus* genome consensus map.

Method for the Selection of a Mutant Carrying Ms Mutation

The invention further provides a method for the selection of mutant plants of leaf chicory that are homozygous or heterozygous for a mutation inducing nuclear recessive male sterility (ms). The method, which is based on the detection of the molecular marker E02M09/163, includes the following steps:

genotyping the chicory plants, leaves or parts thereof by analysing their DNA for the simple sequence repeat (TC)n in SEQ ID NO 1 or SEQ ID NO 2;

comparing the genotypes thus obtained to a male sterile genotype of reference (msms) for said simple sequence repeat (TC)n target DNA regions; and selecting the plants having at least one marker allele of said DNA repeat where n is equal to the n of said male sterile genotype of reference.

The method herein described is based on the tight genetic linkage between the marker E02M09/163, and the locus wherein the ms mutation of the invention maps.

As explained above, the two loci map in the same linkage group and are at an estimated distance of about 6 cM. With a very low error, hence, the mutants selected with the method described above will be heterozygous (Msms) or homozygous (msms) for the male sterile mutation.

The possibility of comparison with a msms mutant of reference, by way of example the starting mutant used in the controlled crosses and/or back-crosses in order to generate a male sterile plant with a specific desired final genotype, allows the breeder to follow the presence of the ms trait throughout the segregating generations and to finally obtain, when desired, a new genotype being mutant homozygous for the ms allele having also other selected traits of interest. The new male sterile mutant may differ from the msms mutant of reference by the presence of specific alleles for a certain number of genes of interest.

In an embodiment, the method of the invention can be used to follow the ms trait in breeding programs where several crosses are performed in order to obtain individuals carrying a desired genotype for several genes and where the ms mutation is to be maintained.

The genotyping of the mutant of reference and of the plants under assay can be carried out with any technique known to the skilled person for the detection of polymorphisms for simple sequence repeats. In general, amplification of a DNA region, also called amplicon, including the repeat is carried out and the number of repeats is assessed by several existing techniques.

The term "amplicon" refers, in the present description, to a nucleotide fragment generated by means of PCR amplification of a DNA sample used as template.

Suitable primers for amplification can be readily generated starting from SEQ ID NO 1 or 2 by the aid of freely available or commercial programs for primers design or by standard techniques for the design of amplification primers.

The amplification may be carried out upon DNA extraction from the sample to be analysed, or directly on material collected from the sample diluted or suspended in the PCR mixture. Standard DNA extraction techniques for plants known in the art can be used.

Any known technique suitable for the detection microsatellites repeats can be used without undue burden or use of inventive skill by the skilled person starting from the marker sequences provided. By way of example, amplicons length may be verified, by capillary electrophoresis techniques; by analysis by dissociation curve, by sequencing the amplicons, by electrophoresis of the amplicons on agarose gel or on polyacrylamide gel or by any other technique known to the skilled person.

By "capillary electrophoresis" it is meant an electrophoretic technique envisaging the use of fused silica microcapillary tubing, with an internal diameter comprised between 10 and 100 microns, with a length between 30 and 50 cm. Said tubing is filled with a (gel-like) substance acting as a molecular sieve. The matrix may be polyacrylamide, dimethylacrylamide or other linear polymers, such as polyethylene oxide or hydroxyethyl cellulose.

To increase resolution, as is commonly known to a skilled person, it is possible to act on: percentage of polymer used, time, voltage and temperature at which the electrophoresis run is performed. This type of electrophoresis can be used only in case a fluorescent labelling is available: at capillary level at a certain spot there will be a crack, through which a laser light will transit, able to excite the fluorochromes and induce a response that can be picked up by the detectors.

For carrying out of the methods described herein with data analysis on agarose or acrylamide gel, all techniques known to a person skilled in the art may be used, with no need of a more detailed description of how to prepare the gels and perform the run. In fact, to date such a technique is common knowledge to a person skilled in the art; concentrations of suitable agarose or polyacrylamide, buffer solutions for gel preparation, agarose or polyacrylamide concentrations, buffers for sample loading and gel staining systems are widely described in laboratory manuals, as well as in textbooks, and for the skilled person require no inventive activity, nor undue experimentation.

Once the amplicons are obtained for the samples of interest, they can be analysed as described above and comparison to the reference msms genotype for the marker of the invention can be carried out. Plants sharing at least one allele of the marker of the invention with the msms genotype of reference will be selected.

In an embodiment of the invention, the amplification can be carried out using primers of SEQ ID NO 3 and SEQ ID NO 4, corresponding, respectively, to a stringent forward primer (5'-CTTGGAGGTGTGAGTGATTCT-3') SEQ ID NO 3 and reverse primer (5'-TACGAAACAGCAAAGA-GAGAC-3') SEQ ID NO 4 amplifying SEQ ID NO 2.

When these primers are used, amplification of the molecular marker of interest is obtained and includes a microsatellite showing a perfect dinucleotide repetition of the motif (TC/GA)n.

Suitable experimental conditions for amplification and detection of amplicons are described below. The diagnostic microsatellite (SSR) marker analysis was carried out following an already tested PCR protocol (Ambrosi D. G., Galla G., Purelli M., Barbi T., Fabbri A., Lucretti S., Sharbel T. F. and Barcaccia G. (2010). DNA markers and FCSS analyses shed light on the genetic diversity and reproductive strategy of *Jatropha curcas* L. Diversity, 2: 810-836.) with some changes to adapt it to red chicory templates. The detection was performed with the use of the 5' M13-tailed primer method (Hayden M. J., Nguyen T. M., Whatman A., McMichael G. L., Chalmers K. J. (2008). Application of multiplex-ready PCR for fluorescence-based SSR genotyping in barley and wheat. Molecular Breeding, 21: 271-281.). Amplified DNA fragments were visualized by capillary electrophoresis after amplification reactions performed with the universal M13 primer (the sequence of the tail is the following: 5'-TTGTAAAACGACGGCCAGT-3' (SEQ ID NO:9)) labeled with a HEX, FAM or TAMRA fluorophore (by Life Technologies, www.invitrogen.com). PCR experiments were conducted in a 20 µl total volume, including 10 mM Tris-HCl, 50 mM KCl, 1.5 mM MgCl2, 200 mM of each dNTP, 3 pmol of primer forward, 8 pmol of primer reverse, 6 pmol M13-labeled primer, 1 U Taq DNA polymerase (GE Healthcare) and 25 ng of genomic DNA as template. Amplification reactions were performed in a 9700 Thermal Cycler (Applied Biosystems): the temperature profile consisted of an initial denaturation step of 5 min at 95° C. followed by 40 cycles of 30 sec at 95° C., 30 sec at annealing temperature of 55-58° C., and 30 second at 72° C., followed in turn by 7 min at 72° C. and then held at 4° C. DNA fragment analysis was carried out using a fully automated capillary electrophoresis system (Applied Biosystems 3130) and SSR patterns were visualized and scored in replicated analysis using the software GeneScan® v. 2.1 e Genotyper® v. 2.0 (Applied Biosystems).

In an embodiment of the invention, as stated above, n ranges from 27 to 33 and the amplicons obtained by amplification with the primers of SEQ ID 3 and 4 above are of a size range of about 160-170 bp.

Method for the Production of Male Sterile Seed Parent Plants

The invention also provides a method for the production of mutant male sterile seed parental lines of leaf chicory, including all radicchio biotypes, wherein the male sterility is a nuclear recessive male sterility due to the mutation of a nuclear gene (ms) linked to the marker of the invention, comprising the steps of:

genotyping the chicory plants, leaves or parts thereof by analysing their DNA for the simple sequence repeat (TC)n in SEQ ID NO 1 or SEQ ID NO 2;
  comparing the genotypes thus obtained to a male sterile genotype of reference (msms) for said simple sequence repeat (TC)n target DNA regions; and
  selecting the plants having both marker alleles of said DNA repeat where n is equal to the n of said male sterile genotype of reference.

The method above is hence a method for the selection of male sterile mutants of all forms of leaf chicory, including all radicchio biotypes (belonging to *Cichorium intybus* subsp. *intybus* var. *foliosum*) wherein the male sterility mutation is the nuclear recessive mutation of the invention. Said method allows the selection of desired seed parent plants that, as described above, are plants to be used as female, i.e. plants that need pollination by a pollen donor plant, and that will produce the seeds of the plants of commercial interest.

It is hence clear that the method for making the seed parent of the invention can comprise several hybridization and selection steps relating to other characters and that the monitoring of the ms trait can be carried out at each of said steps if desired, by the method for the selection of a mutant carrying the ms mutation indicated above, wherein the genotyping of the msms reference genotype can be carried out only once in order to determine said genotype.

The method can hence been described as a method for the production of mutant male sterile seed parents of all forms of leaf chicory, including all radicchio biotypes, wherein the male sterility is a nuclear recessive male sterility due mutation of a nuclear gene (ms) linked to the marker of the invention, comprising the steps of:

genotyping the chicory plants, leaves or parts thereof by analysing their DNA for the simple sequence repeat (TC)n in SEQ ID NO 1 or SEQ ID NO 2;
  comparing the genotypes so obtained to a male sterile genotype of reference (msms) for said simple sequence repeat (TC)n target DNA regions;
  selecting plants having at least one allele for said DNA repeat wherein n is equal to the n of said male sterile genotype of reference,
  submitting said plants to hybridization and selection for other traits, repeating said genotyping on said plants and comparing the genotype thus obtained to said genotype of reference, and selecting the plants having both alleles of said sequence repeat where n is equal to the n of said male sterile genotype of reference.

The steps of
selecting plants having at least one allele for said sequence repeat wherein n is equal to the n of said male sterile genotype of reference,
submitting said plants to hybridization and selection for other traits, repeating said genotyping on said plants and comparing the genotype thus obtained to said genotype of reference, can be repeated several times until the desired genotype for the other traits is obtained.

The seed parent is advantageously a male sterile plant, hence the method of the invention allows to set up breeding programs wherein the male sterility mutation of the invention can be followed throughout several controlled crosses until the desired seed parent is obtained said seed parent being, hence, advantageously male sterile.

Method for the Production of F1 Hybrids Heterozygous for the ms Mutation

In a further embodiment, the invention relates to a method for the production of mutant F1 hybrids of all forms of leaf chicory, including all radicchio biotypes (belonging to *Cichorium intybus* subsp. *intybus* var. *foliosum*) wherein said hybrids are fertile and heterozygous for a mutation in a gene inducing nuclear recessive male sterility (ms) linked to the marker of the invention comprising the steps of:
  genotyping the chicory plants, leaves or parts thereof by analysing their DNA for the simple sequence repeat (TC)n in SEQ ID NO 1 or SEQ ID NO 2,
  comparing the genotypes so obtained to a male sterile genotype of reference for said simple sequence repeat (TC)n target DNA regions,
  selecting the plants having both marker alleles of said sequence repeat where n is equal to the n of said male sterile genotype of reference thus obtaining male sterile (msms) seed parent plants,
  selecting the plants having both marker alleles of said sequence repeat where n is different from the n of said male sterile genotype of reference thus obtaining male fertile (MsMs) pollen donor plants, and
  crossing said seed parent plants with said pollen donor plants and collecting the F1 seed thus obtained.

Hence, the invention also provides a method applicable to a full breeding program, wherein the parental plants that will generate the F1 hybrids having the commercial traits of interest, can be tracked for the ms mutation of the invention throughout the whole selection process aimed to obtaining the assembly of all the commercial traits of interest in the parent plants so to generate, in the end, msms seed parents and MsMs pollen donors.

In an embodiment, the method can comprise several hybridization and selection steps relating to other characters and the monitoring of the ms trait can be carried out at each of said steps if desired, by the method for the selection of a mutant carrying the ms mutation indicated above, wherein the genotyping of the msms reference genotype can be carried out only once in order to determine said genotype.

Hence the invention also relates to a method for the production of mutant F1 hybrids of all forms of leaf chicory, including all radicchio biotypes (belonging to *Cichorium intybus* subsp. *intybus* var. *foliosum*) wherein said hybrids are fertile and heterozygous for a mutation in a gene inducing nuclear recessive male sterility (ms) comprising the steps of:
  genotyping the chicory plants, leaves or parts thereof by analysing their DNA for the simple sequence repeat (TC)n in SEQ ID NO 1 or SEQ ID NO 2;
  comparing the genotypes thus obtained to a male-sterile genotype of reference (msms) for said simple sequence repeat (TC)n target DNA regions,
  selecting plants having at least one allele for said sequence repeat wherein n is equal to the n of said male sterile genotype of reference,
  submitting said plants to hybridization and selection for other traits, repeating said genotyping on said plants and comparing the genotype thus obtained to said genotype of reference,
  selecting the plants having both marker alleles of said sequence repeat where n is equal to the n of said male sterile genotype of reference thus obtaining male sterile (msms) seed parent plants,
  selecting the plants having both marker alleles of said sequence repeat where n is different from the n of said male sterile genotype of reference thus obtaining male fertile (MsMs) pollen donor plants, and
  crossing said seed parent plants with said pollen donor plants and collecting the F1 seed thus obtained.

The steps of
selecting plants having at least one marker allele for said sequence repeat wherein n is equal to the n of said male sterile genotype of reference,
submitting said plants to crossing and selection for other traits, repeating said genotyping on said plants and comparing the genotype thus obtained to said genotype of reference, can be repeated several times until the desired genotype for the other traits is obtained.

The methods of the invention have a very low probability of error as their reliability is of about 95%, hence they are highly effective in the ms mutation selection as explained above.

All the methods herein disclosed can be carried out as described above, hence by amplification of the marker comprising SEQ ID NO 1 or SEQ ID NO 2 (or consisting of SEQ ID NO 2) and determination of the number n of the SSR or simple sequence repeat (TC)n for each allele in the plants or parts thereof assayed and in the msms mutants (wherein the mutation is the mutation of the invention, linked to the marker comprising SEQ ID NO 1 or SEQ ID NO 2) of reference.

As stated above, suitable primers are represented by the primers of SEQ ID NO 3 and SEQ ID NO 4 wherein the PCR conditions can be the ones described above.

All the wild type or male sterile products obtainable by the methods herein described are objects of the present invention.

The following examples are for a better understanding of the invention and not for the limitation thereof.

EXAMPLES

Plant Materials

Four distinct but genetically related male sterile mutants of leaf chicory were recently induced by standard mutational techniques and were isolated on the basis of morphological observations of anthers (FIG. 1). The male-sterile mutants analyzed in this study were named L11ms, IG9 ms, CS1ms and CS2 ms. It is worth mentioning that the male sterile mutants were discovered within local varieties of Radicchio stemmed from recurrent phenotypic selection programs. In particular, the three populations from which they originate have been bred through genetic selection based on progeny tests performed using mother plants chosen for uniformity and superiority of their morphological and agronomic traits.

Cytological Analysis of Male Sporogenesis and Gametogenesis in Radicchio (Leaf-Chicory) Male-Sterile Mutants The presence of pollen within anthers was assayed by whole mount staining with DAPI (4',6-diamidino-2-phenylindole), a fluorescent stain that binds strongly to A-T rich regions in DNA. Anther heads isolated from five flowers for each of the male-sterile mutants and the wild-types were squashed on a microscope slide and treated with 10 µl of staining solution (DAPI 5 µg/ml). After an incubation of 10 min, a detailed observation of stained anthers was done by a Leica DM4000B imagine microscope using the appropriate filter combination for DAPI fluorescent detection. Pictures were taken by the Leica DC300F camera and digital images at 10× or 20× magnification were screened in great details for the presence vs. absence of pollen grains using Adobe Photoshop® CS4 (Adobe Inc., U.S.A., www.adobe.com/it/products/photoshop).

An alternative staining technique was used to investigate the pattern of micro-sporogenesis and the development of pollen grains in each male-sterile mutant in comparison with wild-type. Flowers at four different developmental stages, spanning from young buds to full anthesis, were collected from mutants and wild-type plants, fixed in Carnoy's solution (ethyl alcohol-acetic acid 3:1) and stored at +4° C. for 24-48 hours. After this pre-treatment, flowers were transferred in 70% ethyl alcohol at +4° C. until their use for cytological analysis. Anthers were dissected from individual flowers, opened on microscope slides using a pair of teasing needles with the aid of a stereomicroscope. Specimens containing pollen mother cells, tetrads, microspores and pollen grains were squashed using a drop of 4% acetocarmine and mounted in lacto-phenol with acid fuchsin.

For the preparation of meiocyte chromosomes, anther specimens of mutants and wild-types were treated with citrate buffer (10 mM citric acid, 10 mM sodium citrate, pH 4.5) for 3 min and incubated in a six times diluted pectolytic enzyme mixture containing 1% pectolyase Y23, 1% cellulase RS and 1% cytohelicase (Sigma Aldrich, http://www.sigmaaldrich.com) in 10 mM citrate buffer at 37° C. for about 1-2 hours, according to the anther stage. Anther preparations were squashed on microscope slides using a drop of purified and deionized water (Milli-Q Integral Water Purification System, http://www.millipore.com) and then transferred on a hot plate at 45° C. Cells were spread on microscope slides using a teasing needle by adding one drop of 45% acetic acid, then maintained at 45° C. for 2 min and washed with Carnoy's solution. Each slide was dried on the hot plate at 45° C. and specimens were stained with DAPI.

Cytological observations of male meiosis and gametogenesis as well as karyological analysis of meiocyte chromosomes were made under natural and fluorescent light using a photomicroscope (Zeiss Axiophot photomicroscope, www.zeiss.com) equipped with epifluorescence illumination and single-band filters for DAPI. Photograph films were scanned at 1,200 dpi for digital image processing with Adobe Photoshop® CS4 (Adobe Inc., U.S.A.).

Genetic Analysis of Mutants and Inheritance of Male-Sterility in Radicchio (Leaf Chicory)

Each of the male sterile mutants was crossed as seed parent with a wild type pollinator belonging to the same population. Several F1 plants from each hybrid population were then selfed and crossed in pair-wise combinations in order to obtain segregating F2 progenies. Moreover, F1 plants were also backcrossed as pollen donors with either male sterile mutants belonging to F2 progenies or wild type plants of S1 progenies stemmed from selfing in order to obtain segregating BC1 progenies (FIG. 2). The experimental populations segregating for the male sterility/fertility trait were composed of about 100 plants for each of the four mutants. These populations were used for genetic analyses in order to establish the inheritance pattern of the mutation (e.g., dominant/recessive nuclear vs. cytoplasmic) and to finely map the male sterility gene using microsatellite markers.

Molecular Mapping of the Gene for Male-Sterility in Radicchio (Leaf Chicory)

A total of 118 F2 progeny plants and 92 BC1 progeny plants segregating, respectively, 3:1 and 1:1 for the male fertility vs. sterility trait were used for mapping the ms locus using SSR markers. The F2 plants derived from the progenies of mutants CS1ms and CS2 ms, while the BC1 progenies included plants of mutants L11ms. Moreover, 100 plants of the segregating progenies of mutant IG9 ms were also analyzed in order to validate molecular markers tightly co-segregating with male sterility.

Total genomic DNA was isolated from 100 mg of fresh leaf tissue using the DNeasy® Plant mini-kit (QIAGEN, www.qiagen.com) following the recommendations of the manufacturer. The DNA pellets were washed twice with 70% ethanol, dried and resuspended in 100 µl of TE 0.1× buffer (Tris-HCl 100 mM, EDTA 0.1 mM pH 8). The quality of DNA samples was assessed by electrophoresis on 0.8% (p/v) agarose gels, and its concentration was determined by optical density reading (DU650 spectrophotometer, Beckman) at 260 nm (1 O.D.=50 µg/ml). The purity was calculated by the O.D.260/O.D.280 ratio and by O.D.210-O.D.310 pattern (as described in Barcaccia G., Pallottini L., Soattin M., Lazzarin R., Parrini P. and Lucchin M. (2003). Genomic DNA fingerprints as a tool for identifying cultivated types of radicchio (Cichorium intybus L.) from Veneto, Italy. Plant Breeding 122, 178-183.).

A subset of 48 progeny plants with a contrasting microgametogenesis pattern, (i.e., 24 male sterile plants and 24 male sterile plants) were selected and used for performing a bulked segregant analysis, BSA in the attempt to identify molecular markers linked to the male-sterility trait. Genomic DNA bulks of 12 plants each from two progeny sets were prepared by combining equal amounts of DNA from male fertile and male sterile plants. All bulked DNA samples were investigated by AFLP markers using the parental lines as controls.

Genomic AFLP fingerprinting was performed using the protocol of Vos et al. (1995) (Vos P., Hogers R., Bleeker M., Reijans M., Van de Lee T., Homes M., Frijters A., Pot J., Peleman J, Kuiper M. and Zabeau M. (1995). AFLP: A new technique for DNA fingerprinting. Nucleic Acids Research, 23: 4407-4414.) with modifications described by Barcaccia et al. (2003) (Barcaccia G., Pallottini L., Soattin M., Lazzarin R., Parrini P. and Lucchin M. (2003). Genomic DNA fingerprints as a tool for identifying cultivated types of radicchio (Cichorium intybus L.) from Veneto, Italy. Plant Breeding, 122: 178-183.). AFLP analysis was based on the detection of EcoRI-MseI genomic restriction fragments by PCR amplification with 9 different primer combinations having three selective nucleotides (E+CAC, E+CCA, E+CTG and M+ATC, M+AGG and M+AAG), chosen during preliminary tests according to their ability to find homologous binding sites in red chicory templates. Briefly, after restriction of 500 ng of genomic DNA with EcoRI and MseI endonucleases, pre-amplification reactions were performed in a final volume of 20 µl with EcoRI and MseI primers carrying one selective nucleotide. Then, 20 cycles were carried out at 94° C. for 30 s, 56° C. for 60 s and 72° C. for 60 s in a thermal cycler GeneAmp® System 9700 (Applied Biosystems). The EcoRI primer was labelled by phosphorylating the 5' end with [γ-33P]ATP and T4 kinase, incubating the reaction at 37° C. for 1 h, as described in the manufacturer's instructions. The pre-amplified DNA was diluted 1:1 in Tris-EDTA buffer and was used as template for hot-PCRs with a MseI primer carrying three selective nucleotides in combination with a EcoRI radiolabelled primer, carrying two selective nucleotides at the 3' end. Selective amplification was carried out under cycling conditions which begins with one cycle at 94° C. for 30 s, 65° C. for 30 s, and 72° C. for 60 s. The annealing temperature was then reduced each cycle by 0.7° C. according to a touch-down profile of 13 cycles to reach the optimal annealing temperature of 56° C. Twenty-three cycles were run to complete the final amplification at 94° C. for 30 s, 56° C. for 30 s and 72° C. for 60 s.

After amplification, PCR reactions were stopped with equal volume of loading buffer (98% formamide, 10 mM EDTA, 0.025% bromophenol blue, 0.025% xylene cyanol) and denatured at 94° C. for 5 min. The labelled, restricted and selectively amplified DNA fragments were separated by electrophoresis on 5% denaturing polyacrylamide gels with 8 M urea at 80 W constant power using a standard DNA sequencing unit Sequi-Gen GT-system (BIO-RAD). Gels were dried at 80° C. for 1 h and then visualized by autoradiogram after overnight exposure on an X-ray film at −80° C. using intensifying screens. The AFLP fragment analysis was performed using the 1D® Image analysis software (Kodak Digital Science). Overall data were recorded as a binary matrix by assigning the molecular weight to each quantitatively polymorphic marker identified by comparing DNA fingerprints with known DNA ladders.

Microsatellite (SSR) loci analysis was carried out following an already tested PCR protocol (Ambrosi D. G., Galla G., Purelli M., Barbi T., Fabbri A., Lucretti S., Sharbel T. F. and Barcaccia G. (2010). DNA markers and FCSS analyses shed light on the genetic diversity and reproductive strategy of *Jatropha curcas* L. Diversity, 2: 810-836.) with some changes to adapt it to red chicory templates. The detection was performed with the use of the 5' M13-tailed primer method (Hayden et al., 2008) (see Hayden M. J., Nguyen T. M., Whatman A., McMichael G. L., Chalmers K. J. (2008). Application of multiplex-ready PCR for fluorescence-based SSR genotyping in barley and wheat. Mol. Breeding, 21: 271-281.). DNA fragments were visualized by capillary electrophoresis after amplification reactions performed with the universal M13 primer (the sequence of the tail is the following: 5'-TTGTAAAACGACGGCCAGT-3' (SEQ ID NO:9)) labeled with a HEX, FAM or TAMRA fluorophore (by Life Technologies). PCR experiments were conducted in a 20 µl total volume, including 10 mM Tris-HCl, 50 mM KCl, 1.5 mM MgCl2, 200 mM of each dNTP, 3 pmol of primer forward, 8 pmol of primer reverse, 6 pmol M13-labeled primer, 1 U Taq DNA polymerase (GE Healthcare) and 25 ng of genomic DNA as template. All individual DNA samples were then investigated with 9 SSR markers belonging to as many mapped loci, one for each of the nine linkage groups (i.e., basic chromosomes) of the genetic map recently constructed by Cadalen et al. (2010) Amplification reactions were performed in a 9700 Thermal Cycler (Applied Biosystems): the temperature profile consisted of an initial denaturation step of 5 min at 95° C. followed by 40 cycles of 30 sec at 95° C., 30 sec at annealing temperature of 55-58° C., and 30 second at 72° C., followed in turn by 7 min at 72° C. and then held at 4° C. DNA fragment analysis was carried out using a fully automated capillary electrophoresis system (Applied Biosystems 3130) and SSR patterns were visualized and scored in replicated analysis using the software GeneScan® v. 2.1 e Genotyper® v. 2.0 (Applied Biosystems).

As a preliminary screening based on SSR markers, 12 male sterile and 12 male fertile genomic DNA plants were randomly selected from segregating populations of each mutant, for a total of 96 plants. For the marker alleles showing to significantly co-segregate with the male-sterility/fertility genotypes, the analysis was extended to all the 300 plants available on the whole for this study. The observed segregation ratio of SSR markers was tested by chi-square analyses for goodness-of-fit to the expected 3:1 or 1:1 segregation ratios, as well as for independent assortment in the male-sterile vs. wild-type progenies by a 2×2 contingency test. Segregation data for the markers were analyzed with JOINMAP® v. 2.0 (Stam P. and Van Ooijen J. W. (1995). JOINMAP™ version 2.0: Software for the calculation of genetic linkage maps. CPRO-DLO, Wageningen, The Netherlands.) using the cross pollination (CP) population type option (i.e., segregating populations resulting from a cross between two heterogeneous parents that were heterozygous and/or homozygous at the loci being tested). The association between microsatellite markers and male sterility was assessed by recording the target ms locus as a putative monogenic marker fully co-segregating with the trait being mapped. For the genotype code option, presence of marker allele and wild-type phenotype were assigned to aa=homozygous dominant or ab=heterozygous, and absence of marker allele and male-sterile phenotype to bb=homozygous recessive. For the identification of the linkage group carrying the ms locus with the selected SSR markers, the grouping module was applied by setting a minimum LOD=3 and a maximum recombination frequency, r=30% (Barcaccia G., Albertini E., Rosellini D., Tavoletti S. and Veronesi F. (2000). Inheritance and mapping of 2n egg production in diploid alfalfa. Genome, 43: 528-537.). The genetic distance between each pair-wise comparison of SSR marker locus and ms locus, expressed in centimorgans (cM), was calculated from the recombination frequency corrected by using the Kosambi's mapping function (Kosambi (1944). The estimation of map distances from recombination values. Ann. Eugen., 12: 172-175.).

Experimental Conditions for Amplification and Detection of Amplicons

The diagnostic microsatellite (SSR) marker analysis was carried out following an already tested PCR protocol (see Ambrosi et al., 2010) with some changes to adapt it to red chicory templates. The detection was performed with the use of the 5' M13-tailed primer method (see Hayden et al., 2008). DNA fragments were visualized by capillary electrophoresis after amplification reactions performed with the universal M13 primer (the sequence of the tail is the following: 5'-TTGTAAAACGACGGCCAGT-3' (SEQ ID NO:9)) labeled with a HEX, FAM or TAMRA fluorophore (by Life Technologies, www.invitrogen.com). PCR experiments were conducted in a 20 µl total volume, including 10 mM Tris-HCl, 50 mM KCl, 1.5 mM MgCl2, 200 mM of each dNTP, 3 pmol of primer forward, 8 pmol of primer reverse, 6 pmol M13-labeled primer, 1 U Taq DNA polymerase (GE Healthcare) and 25 ng of genomic DNA as template Amplification reactions were performed in a 9700 Thermal Cycler (Applied Biosystems): the temperature profile consisted of an initial denaturation step of 5 min at 95° C. followed by 40 cycles of 30 sec at 95° C., 30 sec at annealing temperature of 55-58° C., and 30 second at 72° C., followed in turn by 7 min at 72° C. and then held at 4° C. DNA fragment analysis was carried out using a fully automated capillary electrophoresis system (Applied Biosystems 3130) and SSR patterns were visualized and scored in replicated analysis using the software GeneScan® v. 2.1 e Genotyper® v. 2.0 (Applied Biosystems).

Linkage of the DNA Marker Comprising SEQ ID NO 1 with the Male Sterile Mutant of the Invention The AFLP-derived amplicons corresponding to the marker E02M09/230 identified and characterized in the chicory progenies were recovered from the agarose gels, subcloned into plasmid vectors and sequenced in order to obtain information on the whole genomic sequence. PCR reactions were performed for both strands using three genomic DNA templates belonging to male sterile and male fertile plants of each segregating population. The sequence of the SCAR marker developed from the AFLP amplicon genetically linked with the male sterility trait, that correspond to the DNA marker E02M09/163, is the following:

```
CTTGGAGGTGTGAGTGATTCTCGGAGAGTT(TC)nCAGAGATCATTGCT
TTGGTAATTCTCGCTGATTTCAGTTCATTGTCGTCTCTTTGCTGTTT
CGTA (SEQ ID NO: 6).
```

The molecular marker of interest proved to include a microsatellite showing a perfect dinucleotide repetition of the motif (TC/GA)n, with n ranging from 27 to 33 (SEQ ID NO:7). As a consequence, a novel SSR assay for the detection of this marker, which includes the basic dinucleotide repeat TC/GA and whose size ranges from 141-171 bp in relation to the genotypes, was implemented by the design of a specific and stringent forward primer (5'-CTTGGAG-GTGTGAGTGATTCT-3'(SEQ ID NO:3)) and reverse primer (5'-TACGAAACAGCAAAGAGAGAC-3' (SEQ ID NO:4)).

Figure 7:
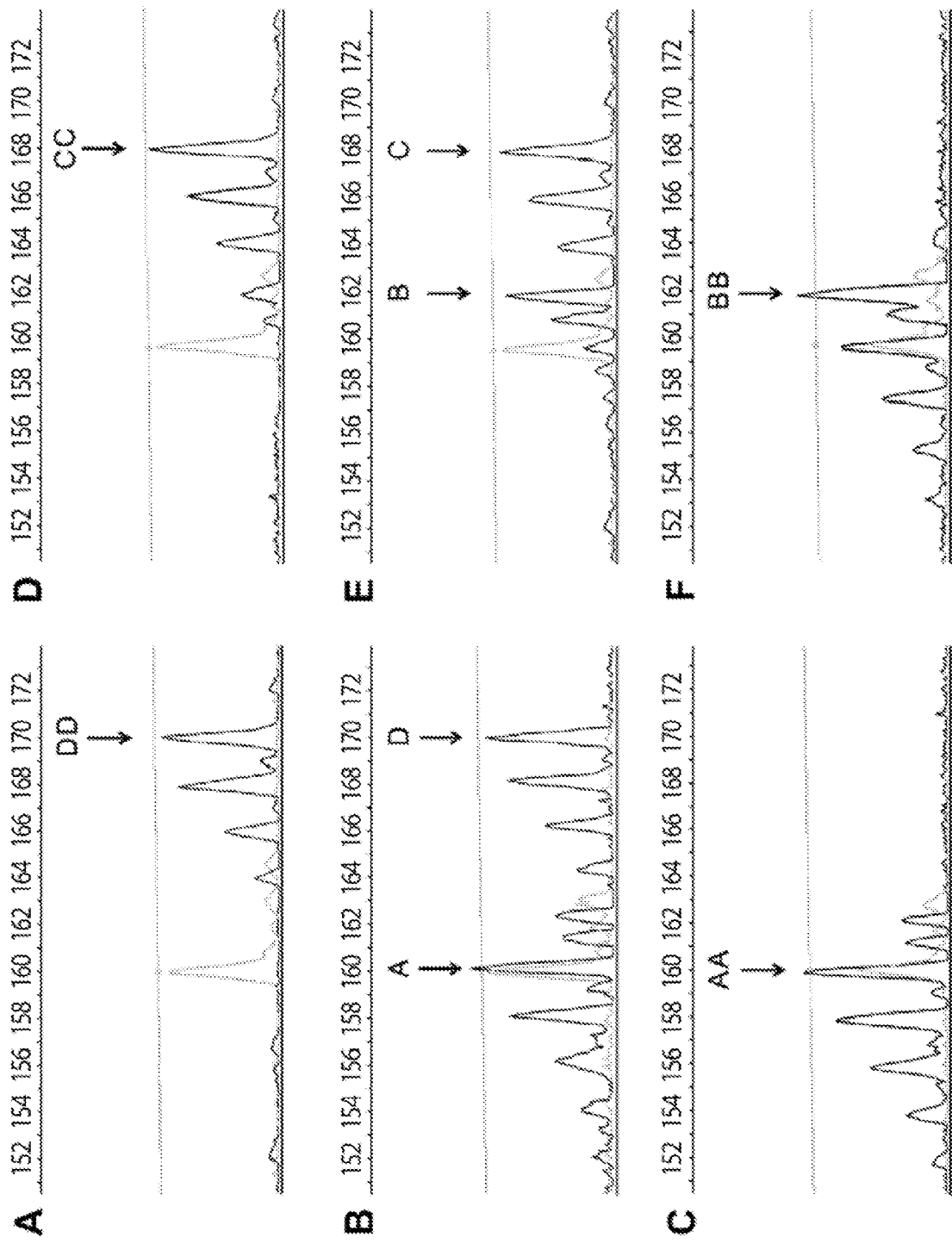
FIG. 7: Molecular SSR marker diagnostic assay for discriminating male sterile from male fertile plant genotypes. The male sterile plants of reference in the assay are homozygous AA or BB, with marker alleles of 27 and 28 TC repeats (n=27 or 28), respectively, whereas male fertile-plants observed were either heterozygous AD or BC and homozygous DD or CC, with marker alleles of 33 and 32 TC repeats (n=33 or 32), respectively. This SSR assay is useful as a tool of marker-assisted selection for an early screening of the male sterile plants within segregating progenies, with a genotyping error around 2.9%.

FIG. 7 shows SSR genotypes detected in the progeny plants of segregating populations: male-sterile plants were homozygous AA or BB, with marker alleles of 160 and 162 bp, respectively, whereas male fertile-plants could be either heterozygous AD or BC and homozygous DD or CC, with marker alleles of 170 and 168 bp, respectively. We concluded that the SSR assay developed in this study can be profitably adopted as a tool of marker-assisted breeding and exploited for an early screening of the T&T® male-sterile plants within segregating progenies stemmed from backcrosses with a genotyping error around 2.9%.

Association of the DNA Markers Comprising SEQ ID NO 1 and SEQ ID N05 with the Linkage Group 4 of the Cichorium intybus Consensus Map The assignment of the ms gene, whose mutation is responsible for male-sterility in Radicchio (leaf chicory), to the linkage group 4 of the consensus genetic map of Cichorium intybus was obtained by testing the co-segregation of mapped molecular markers with the mutant phenotype in F2 and BC1 experimental populations. In particular, we assayed a total of 9 specifically selected marker loci so to have one reference SSR marker for each of the nine linkage groups of Cichorium intybus (Cadalen T., Mörchen M., Blassiau C., Clabaut A., Scheer I., Hilbert J-L., Hendriks T. and Quillet M-C. (2010). Development of SSR markers and construction of a consensus genetic map for chicory (Cichorium intybus L.). Molecular Breeding, 25: 699-722). The 20-mer forward and reverse primers used for assaying the SSR locus coded as EU03H01, containing an imperfect microsatellite motif (TG)nCG (TG)n, and found associated to the linkage group 4 of the Cichorium intybus consensus map are the following: 5'-GCCATTCCTTTCAAGAGCAG-3' (SEQ ID NO:10) and 5'-AACCCAAAACCGCAACAATA-3' (SEQ ID NO:11) (Cadalen T., Mörchen M., Blassiau C., Clabaut A., Scheer I., Hilbert J-L., Hendriks T. and Quillet M-C. (2010). Development of SSR markers and construction of a consensus genetic map for chicory (Cichorium intybus L.). Molecular Breeding, 25: 699-722).

Scientific Data and Results

Male-Sterility of Leaf Chicory Mutants is Controlled by a Nuclear Gene that Acts as Recessive Three distinct inheritance models for the genetic basis of male-sterility could be postulated for the male sterile mutations of red chicory: cytoplasmic, related to a mitochondrial gene, and nuclear, which can be associated to either a dominant or a recessive gene. In case of cytoplasmic origin, F1 progenies had to be composed exclusively of male sterile plants (with cytoplasm of S type), whereas in case of nuclear origin, two were the expected results: all F1 progeny plants (with a heterozygous genotype Msms) had to manifest male-sterility, for a trait controlled by a dominant Mendelian factor (i.e., Ms), or male-fertility, for a trait controlled by a recessive Mendelian factor (i.e., ms).

All crosses between male-sterile mutants and wild-type pollinators resulted in 100% male-fertile F1 progenies, whereas F2 and BC1 progenies showed to segregate for this trait and to be composed of both male-fertile and male-sterile plants, with proportions equal to 3:1 and 1:1, respectively. These findings suggested that the male-sterile mutants used as seed parents are homozygous recessive at the locus responsible for male-sterility (i.e., msms) and that the wild-type pollinators are homozygous for the dominant allele accounting for male-fertility (i.e., MsMs). Segregation ratios observed in the F2 and BC1 progenies developed for each of the four male-sterile mutants along with chi-square values are reported in Table 1. Overall data clearly support a nuclear origin and a monogenic control of recessive type for the male-sterility trait in each of the red chicory mutants. Taking together all segregating progeny sets of the F2 and BC1 populations, which included 383 and 380 plants respectively, chi-squares values were non-significant, being as low as 1.324 and 0.095 (Table 1). It is worth mentioning that all flowering plants could be easily scored as male-fertile or male-sterile by a rapid observation of squashed anthers and pollen grains stained with aceto-carmine under a stereomicroscope. No doubtful cases of classification were ever experienced.

TABLE 1

Segregation ratios observed in the F2 and BC1 populations bred for each of the male-sterile mutants along with chi-square values.

| | | | Expected ratios | | Observed ratios | | |
|---|---|---|---|---|---|---|---|
| Mutants | Progeny type | Progeny size | male-fertile plants | male-sterile plants | male-fertile plants | male-sterile plants | Chi-square values |
| CS1ms | F2 | 107 | 80 | 27 | 82 | 25 | 0.153 |
| CS2ms | F2 | 92 | 69 | 23 | 71 | 21 | 0.232 |
| IG9ms | F2 | 100 | 75 | 25 | 78 | 22 | 0.480 |
| L11ms | F2 | 84 | 63 | 21 | 66 | 18 | 0.571 |
| Overall | F2 | 383 | 287 | 96 | 297 | 86 | 1.324 |
| CS1ms | BC1 | 94 | 47 | 47 | 49 | 45 | 0.170 |
| CS2ms | BC1 | 102 | 51 | 51 | 54 | 48 | 0.353 |

TABLE 1-continued

Segregation ratios observed in the F2 and BC1 populations bred for each of the male-sterile mutants along with chi-square values.

| Mutants | Progeny type | Progeny size | Expected ratios | | Observed ratios | | Chi-square values |
|---|---|---|---|---|---|---|---|
| | | | male-fertile plants | male-sterile plants | male-fertile plants | male-sterile plants | |
| IG9ms | BC1 | 88 | 44 | 44 | 41 | 47 | 0.409 |
| L11ms | BC1 | 96 | 48 | 48 | 43 | 53 | 1.042 |
| Overall | BC1 | 380 | 190 | 190 | 187 | 193 | 0.095 |

In the Mutants Male Gametogenesis is Arrested at the Stage of Uninucleate Microspores Regular meiosis was normally found in wild-type plants. After meiosis, each microspore of the tetrads was shown to develop into a binucleate pollen grain through a mitotic division that originated a vegetative and a generative nucleus. Moreover, at anthesis when the pollen grains were mature, they germinated and emitted the pollen tubes (i.e., the microgametophyte), in which the generative nucleus underwent another mitotic division, giving rise to two distinct sperm nuclei.

Figure 3:
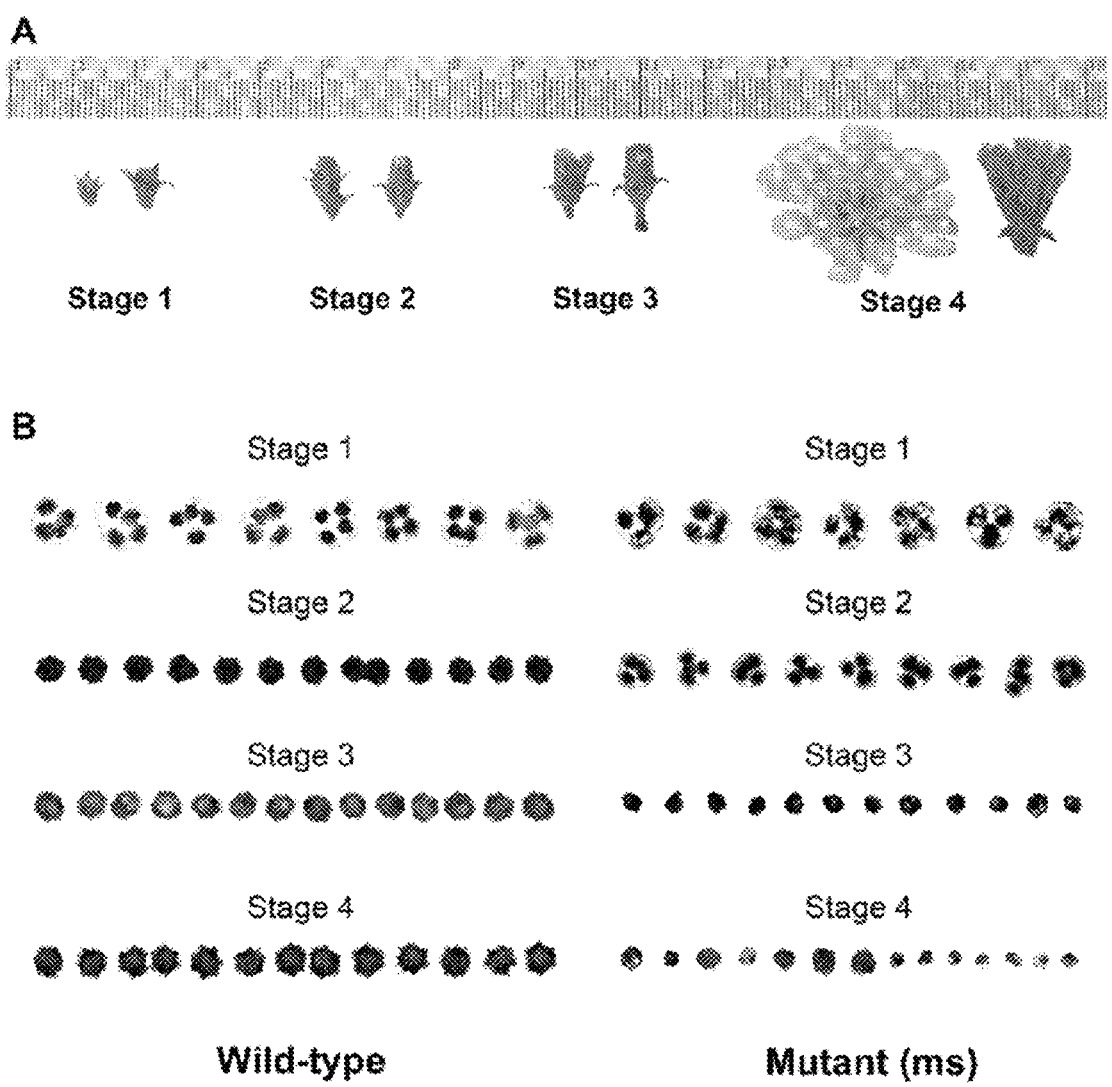
FIG. 3: Flower developmental stages in red chicory (panel A) and patterns of male gametogenesis in the male-sterile mutants in parallel with wild-type plants (panel B). In the mutants, the microspores of each tetrad arrest their development at the uninucleate stage, degenerating before their release from the tetrads. At full flowering, most of the microspores of dehiscent anthers were found shapeless, shrunken and much smaller than wild-type ones.
Figure 4:
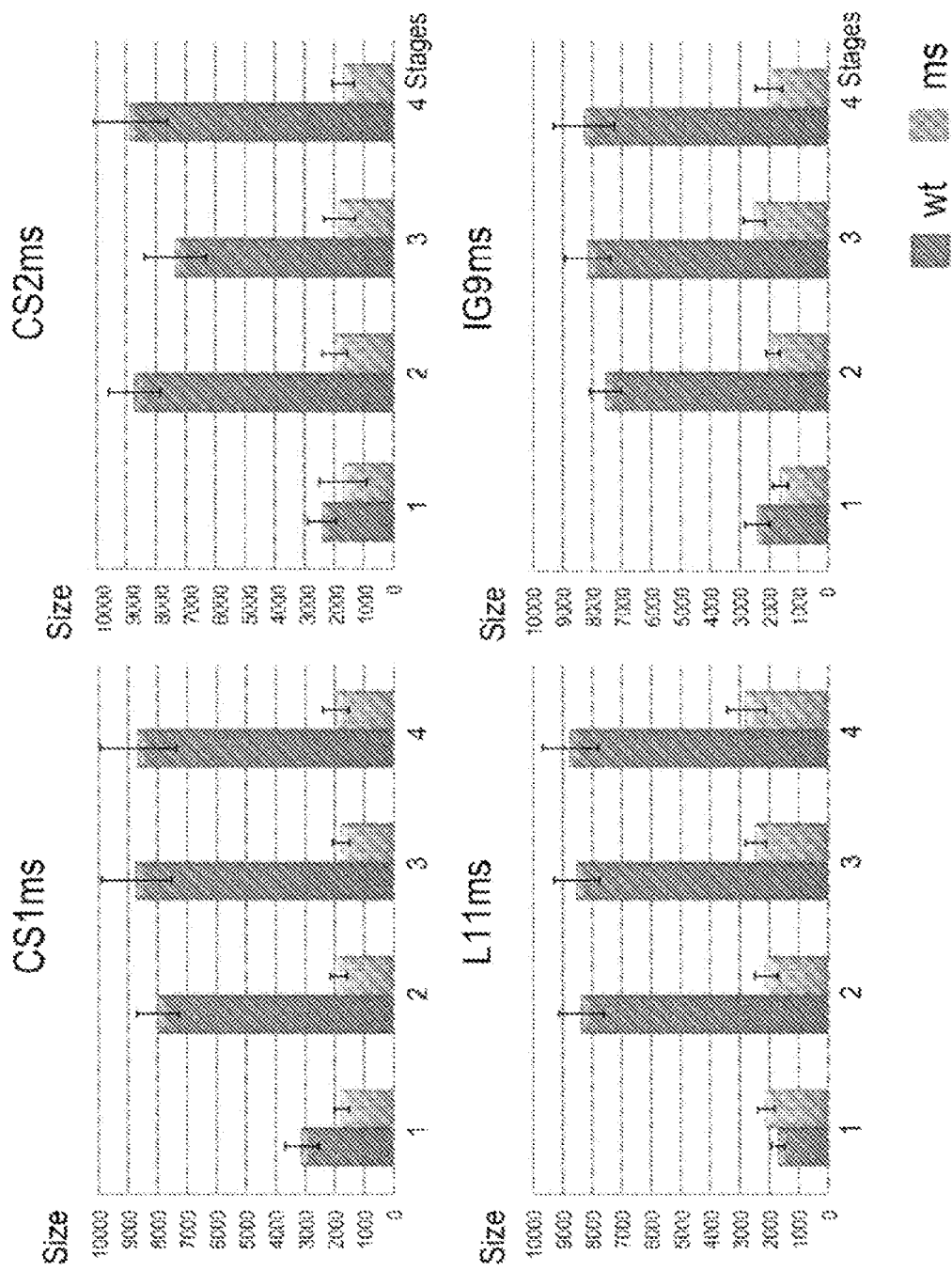
FIG. 4: Microspore size in the male-sterile mutants compared to wild-type plants, expressed as mean value (histograms) with standard error (bars). At the stage of tetrad, the microspores were comparable for their size and shape between mutants and wild-types, whereas mutant microspores at the uninucleate stage proved to be about three times smaller than wild-type ones.

In the male-sterile mutants, the cytological analysis showed that microsporogenesis proceeds normally up to the development of microspore tetrads. Then the microspores arrested their development at the uninucleate stage, as documented in FIG. 3 using a parallel with unrelated wild-type plants. In particular, cytological observations revealed that microspores degenerate before their release from the tetrads showing a collapse of the exine. At the end of male meiosis, most of the microspores were found arranged in tetrads while some others were released, becoming shapeless even though the cytoplasm stained well with acetocarmine. At the beginning of gametogenesis, non-viable shrunken microspores were clearly visible within anthers (details given on FIG. 3). It is worth mentioning that microspore tetrads were comparable for their size and shape between mutants and wild-types, whereas mutant microspores at the uninucleate stage proved to be shrunken and much smaller than wild-type ones, as shown on FIG. 4. Above all, pollen grains were never detected in mature anthers of all four male sterile mutants. This cytological finding was also supported by DAPI staining of squashed anthers (see FIG. 1, panels C-D and G-H).

Figure 5:
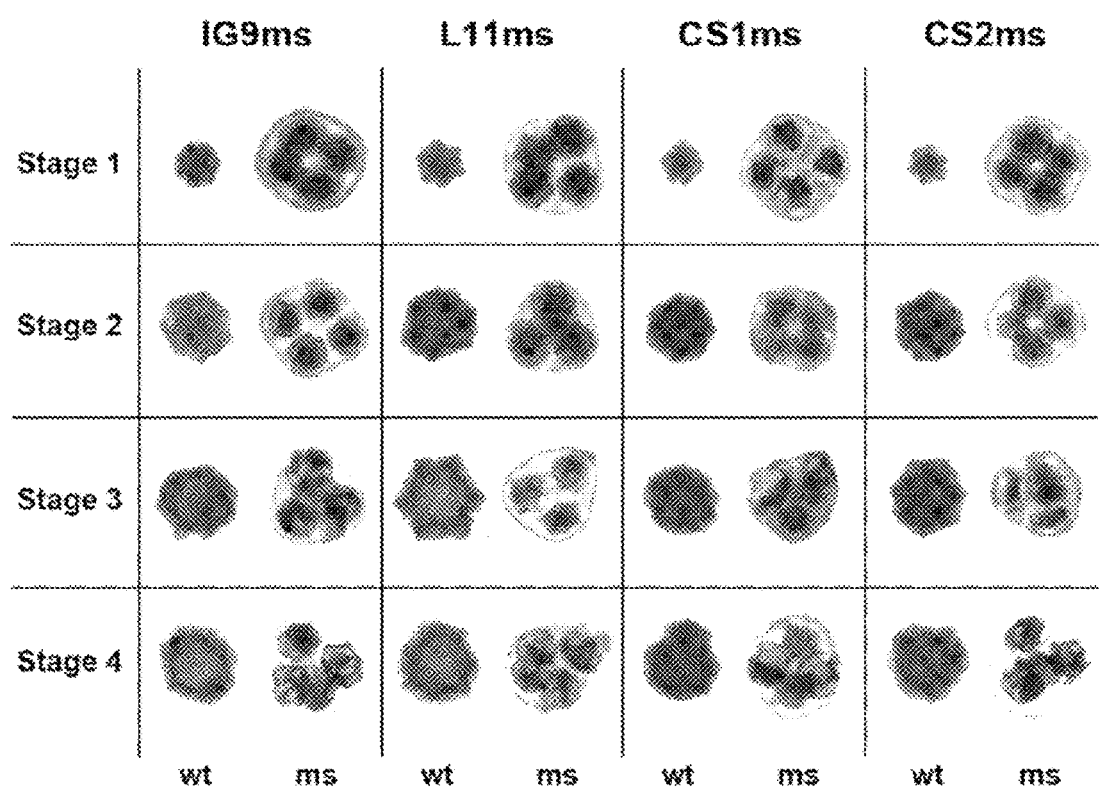
FIG. 5: Parallel between male gametogenesis in wild-type plants and male-sterile mutants belonging to segregating progenies at flower stages 1-4. Gametogenesis followed a regular pathway in male-fertile plants, giving rise to mature pollen grains, whereas microspores collapsed within each tetrad in the male-sterile plants, without any further developing process. This finding demonstrated that the gene responsible for male-sterility is inherited in the offspring from each mutant by recovering an unaltered maternal genotype, which is always associated to an unchanged phenotype for male-sterility.

Furthermore, the cytological analysis of microsporogenesis and gametogenesis was performed also in the plants belonging to F2 and BC1 progenies. At the cellular level, male meiosis was shown to proceed regularly until the stage of microspore tetrads in both male-sterile mutants and male-fertile plants. Gametogenesis followed a regular pathway in male-fertile plants, giving rise to mature pollen grains, whereas microspores collapsed within each tetrad in the male-sterile plants, without any further developing process (FIG. 5). In fact, at the end of gametogenesis, a similar phenotype of non-viable shrunken microspores was observed for male-sterile mutants belonging to each of the segregating progenies (FIG. 5). This finding demonstrated that the gene responsible for male-sterility is inherited in the offspring from each mutant by recovering an unaltered maternal genotype which was always found associated to an unchanged phenotype for male-sterility.

Figure 6:
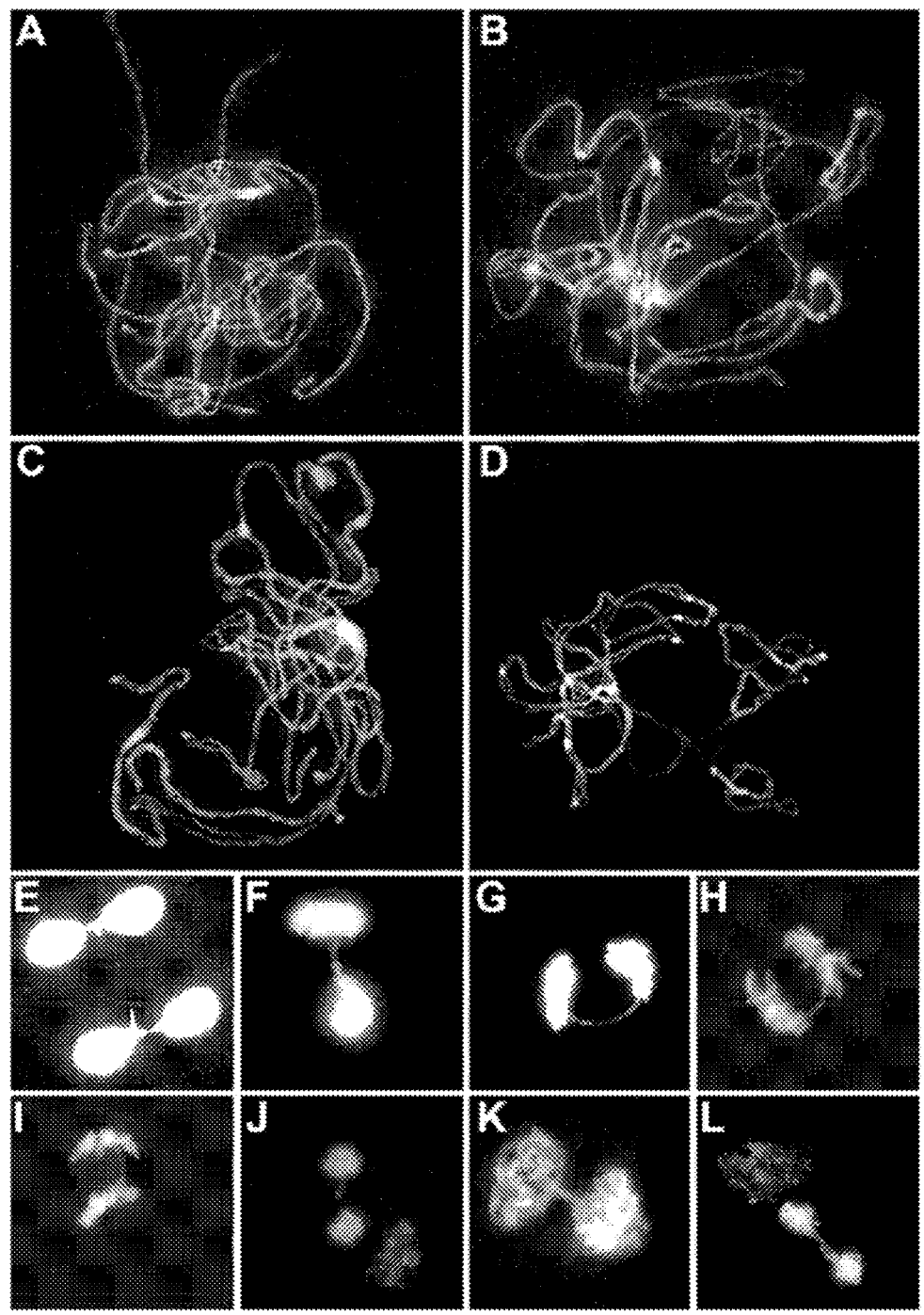
FIG. 6: Results of cytogenetic analyses of male-sterile mutants: different types of meiotic abnormalities were found in the male-sterile mutants compared to wild-types, especially at prophase I, along with chromatin bridges observed in ana-telophase II. Some examples of normal chromosome pairing in wild-types (panel A) and miss-pairing of certain chromosome pairs in male-sterile mutants (panels B-D). The main aberrant feature in the mutants was recovered at pachytene stage when the homologous chromosomes reached their full pairing: homologues were not completely pairing each other and aberrant structures characterized by one or more loops, due to partial or aspecific pairing between homologous chromosomes, were often observed (see white arrows in panels B-D). Moreover, several cases of chromatin bridges, i.e. bridges made of chromatin occurring between newly forming cells, were found in the male-sterile mutants (panels E-L).

The chromosome behaviour of male-sterile mutants was also investigated during meiosis: the male meiocyte chromosomes were further analyzed by means of DAPI staining in both wild-type and mutant flowers. Different forms of meiotic abnormalities were found in the male-sterile mutants compared to wild-types, especially at prophase I. In fact, during pachytene, the stage when chiasmata take place and crossing-over occurs between non-sister chromatids of homologous chromosomes, abnormal pairings and chromosomal loops were observed in several sites. Moreover, chromatin bridges were also observed in ana-telophase II. FIG. 6 shows some examples of normal chromosome pairing in wild-types (panel A) and miss-pairing of certain chromosome pairs in male-sterile mutants (panels B-D). The main aberrant feature was recovered at pachytene stage when the homologue chromosomes reached their full pairing. It was evident that in the mutant, the homologues were not completely pairing each other and aberrant structures characterized by one or more loops, due to partial or aspecific pairing between homologous chromosomes, were often observed (see white arrows in panels B-D of FIG. 6). Moreover, several cases of chromatin bridges, i.e. bridges made of chromatin occurring between newly forming cells, were found in the male-sterile mutants (FIG. 6, panels E-L).

Male Sterility is Genetically Linked to a Microsatellite Marker Mapped on Linkage Group 4 of Chicory and Mutants May be Recognized Using a Molecular Assay at an Early Stage of Development In order to map the ms locus, a subset of F2 progenies was initially screened to find out molecular marker alleles co-segregating with the male-sterility/fertility trait. Then the selected markers were validated using BC1 progenies on the basis of chi-square values against independent assortment patterns. This strategy allowed us to detect a molecular marker qualitatively polymorphic between DNA bulks of male fertile and male sterile progeny plants and to precisely calculate the genetic distance between the male-sterility trait and the co-segregating marker.

The Mendelian factor responsible for male-sterility was found tightly linked with the molecular marker coded as E02M09/230. When the datasets for both the trait and the marker were analyzed together, there was a significant deviation in the segregation data from the expected 1:1:1:1 ratio. The genetic determinant for male-sterility was found tightly associated with the diagnostic marker, as their alleles were preferentially inherited together (Fisher's 2×2 contingency test: $\chi 2=75.3$ with $P<0.0001$). However, recombination events were apparently possible in the chromosome block carrying the male-sterility gene. In fact, this gene was associated with the marker E02M09/230 in a chromosome window likely characterized by active crossing-over sites and densely saturated by expressed sequence tags. The mean recombination frequency between the male-sterility trait and the microsatellite marker was equal to 5.8%, corresponding to about 6 cM after correction with the Kosambi's function. This means that the size of the chromosome window covering the ms locus may be around 3,000 Kb (assuming 500 Kb/cM).

Genetic analysis of the specific SCAR marker containing a (TC/GA)n repeat, with n ranging from 27 to 33 (SEQ ID NO:7), developed from the AFLP-derived amplicon E02M09/230, showed that this sequence repeat is located on linkage group 4 of the consensus map of *Cichorium intybus* L. (Cadalen T., Mörchen M., Blassiau C., Clabaut A., Scheer I., Hilbert J-L., Hendriks T. and Quillet M-C. (2010). Development of SSR markers and construction of a consensus genetic map for chicory (*Cichorium intybus* L.). Molecular Breeding, 25: 699-722.). In particular, this DNA marker belongs to the distal part of linkage group 4 being mapped on a chromosome window of about 6 cM apart from the male-sterility (ms) locus. Among the microsatellite markers publicly available for the chicory genome, the marker locus coded as EU03H01/178 containing an imperfect microsatellite motif (TG)nCG(TG)n, with total n varying up to 11 (SEQ ID NO:8), was found associated to the male-sterility (ms) trait, showing a genetic distance around 13 cM.

Figure 8:
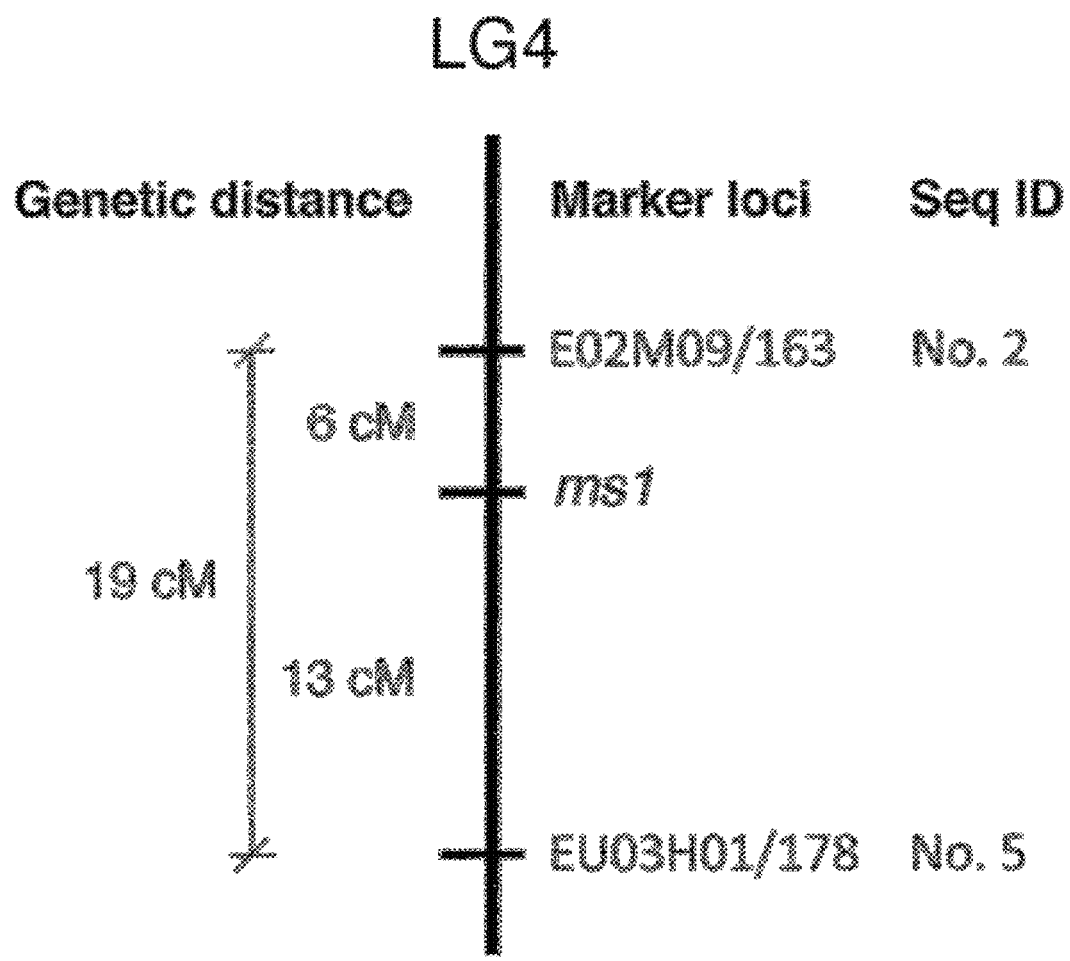
FIG. 8. Schematic representation of part of the linkage group 4 (i.e. LG4) of *Cichorium intybus* consensus map containing DNA markers coded as E02M09/163 and EU03H01/178 associated with the ms locus where the mutant gene responsible for male sterility is located in Radicchio (leaf chicory). Each of these two DNA markers includes a microsatellite repeat in their nucleotide sequences as shown in SEQ ID NO1 and SEQ ID NO 5.

We can therefore establish that the two DNA markers (i.e. E02M09/163 and EU03H01/178) and the ms gene are genetically associated in the same linkage group (i.e. LG4), and that this linkage is such that a chromosome window characterized by a total recombination frequency of 18% can be observed between the two marker loci. As a consequence, the two marker loci enclosing the ms gene are at a genetic distance of about 19 cM (FIG. 8). The probability that both markers genetically recombine from the ms locus because of the occurrence of double crossing-overs is lower 1%.

Non OGM Male Sterility in Chicory and its Use for Breeding Hybrid Populations

The new male-sterility trait obtained and demonstrated by the inventors in chicory mutants is controlled by a single nuclear gene (ms) that acts at the recessive status. In fact, all crosses between male-sterile mutants and wild-type pollinators resulted in 100% male-fertile F1 progenies (Msms), whereas F2 and BC1 progenies segregated for this trait being composed of both male-fertile and male-sterile plants, with ratios equal to 3 (25% MsMs and 50% Msms):1 (25% msms) and 1 (50% Msms):1 (50% msms), respectively.

Documentation that the male gametogenesis is arrested at the stage of microspore tetrads has been herein provided. In all male sterile mutants, the cytological analysis showed that microsporogenesis seems to proceed regularly up to the development of tetrads, then the miscropores arrest their developmental program. At the beginning of microgametogenesis, non-viable shrunken microspores were clearly visible within anthers. Interestingly, meiotic abnormalities were found in the male-sterile mutants, especially at prophase I. In fact, abnormal pairings and chromosomal loops were observed during pachytene. It is well known that the central function of synapsis is the recognition of homologues by pairing, an essential step for a successful meiosis. Irregular synapsis for some of the homologous chromosomes may alter the further development of microspores. This feature would stop the process of male gametogenesis.

Genetic factors affecting meiotic chromosome pairing in plants are of special interest to geneticists and especially breeders. The nuclear male-sterile mutations can affect microsporogenesis or microgametogenesis, hampering the formation of pollen grains. A crucial step for male fertility is the conjugation of chromosomes during the first meiotic prophase, a phenomenon termed synapsis. When synapsis occurs irregularly in the male meiocytes, meiosis may lead to non-functional microspores. Several mutants characterized by the lack of chromosome pairing during the first meiotic prophase (i.e., asynapsis) have been found in plant species, as well as mutants in which chromosomes initially pair in early meiotic prophase but fail to remain paired at later meiotic stages (i.e., desynapsis).

The findings disclosed herein, without being bound to theory, suggest that the exchange of DNA segments over regions of homology is strongly prevented in the male-sterile mutants and that the lack of regular synapsis for some of the homologous chromosomes may alter the further development of microspores. In addition, the occurrence of chromatin bridges between newly forming cells is usually an indicator of abnormalities related to cellular division. All together these features provide karyological evidences that support chromosome features and factors negatively influencing the process of male gametogenesis, resulting in a phenotype that can be described as "anthers with no pollen grains".

It is worth noting that the sterility of gametes occurs only in male organs. The quantity of seeds set by the mutant flowers was not significantly different from that of wild-type plants, demonstrating that the female organs of mutant flowers are completely fertile. As a consequence, the observations herein provided suggest that the mutant phenotype is attributable to a gene expressed in an anther-specific manner A new PCR-based assay that can be profitably adopted for an early screening of the male-sterile plants within segregating progenies has been implemented by the inventors, with a genotyping error lower than 1%. The gene responsible for male-sterility was found genetically linked to a new molecular marker (herein denominated E02M09/230), about 6 cM apart from the ms locus. The molecular marker linked to male-sterility was sequenced and its analysis disclosed a perfect dinucleotide microsatellite of the repetitive motif (TC/GA)n, with n being variable and ranging, in most observed cases, from 27 to 33 (SEQ ID NO:7). As a consequence, an SSR assay for the detection of this marker, whose size ranges around 160-170 bp, was implemented by the design of a specific pair of primers of SEQ ID NO 3 and 4. The male-sterile plants were homozygous for the smaller marker alleles, whereas male fertile-plants could be either heterozygous or homozygous for marker alleles of larger size. The PCR-based assay herein described will find application not only for the marker-assisted selection of male-sterile seed parents but also for the genetic identification and legal protection of these valuable mutant genotypes of red chicory. Since the history of plant breeding after the rediscovery of Mendel's laws, the exploitation of heterosis is an effective approach to increase crop yields. F1 hybrid populations and varieties in major crops such as cereals and vegetables can show more than a 100% yield advantage over the best conventional ones under the same cultivation conditions. Difficulties in breeding elite male sterile lines and producing commercial hybrid seeds hamper the development of F1 hybrid populations. An important role in chicory breeding could be played by male-sterility in hybrid seed production: this is particularly true in "radicchio" since self-incompatibility of parental lines was found inadequate for reliable production of F1 hybrids.

In conclusion, the discovery and analysis of non-engineered male-sterility in this species (i.e., non OGM) will open new frontiers for breeding new F1 populations of radicchio, in particular, and of chicory, in general, provided that such trait can be successfully transferred to elite inbred lines and precociously identified by molecular diagnostic assays suitable to perform marker-assisted selection as from the teachings of the present disclosure.

BIBLIOGRAPHY

Ambrosi D. G., Galla G., Purelli M., Barbi T., Fabbri A., Lucretti S., Sharbel T. F. and Barcaccia G. (2010). DNA markers and FCSS analyses shed light on the genetic diversity and reproductive strategy of *Jatropha curcas* L. Diversity, 2: 810-836.

Barcaccia G., Albertini E., Rosellini D., Tavoletti S. and Veronesi F. (2000). Inheritance and mapping of 2n egg production in diploid alfalfa. Genome, 43: 528-537.

Barcaccia G., Pallottini L., Soattin M., Lazzarin R., Parrini P. and Lucchin M. (2003). Genomic DNA fingerprints as a tool for identifying cultivated types of radicchio (*Cichorium intybus* L.) from Veneto, Italy. Plant Breeding, 122: 178-183.

Cadalen T., Mörchen M., Blassiau C., Clabaut A., Scheer I., Hilbert J.-L., Hendriks T. and Quillet M-C. (2010). Development of SSR markers and construction of a consensus genetic map for chicory (*Cichorium intybus* L.). Molecular Breeding, 25: 699-722.

Denis M., Delourne R., Gourret J. P., Mariani C. and Renerd M. (1993). Expression of engineered nuclear male sterility in *Brassica napus*: genetics, morphology and sensitivity to temperature. Plant Physiology, 101(4): 1295-1304.

Gonthier L, Blassiau C, Mörchen M, Cadalen T, Poiret M, Hendriks T, Quillet M C. (2013). High-density genetic maps for loci involved in nuclear male sterility (NMS1) and sporophytic self-incompatibility (S-locus) in chicory (*Cichorium intybus* L., Asteraceae). Theoretical and Applied Genetics, 126 (8): 2103-2021 (doi: 10.1007/s00122-013-2122-9).

Horn R., Köhler R. H. and Zetsche K. (1991). A mitochondrial 16-kDA protein is associated with cytoplasmic male sterility in sunflower. Plant Molecular Biology, 17: 29-36.

Hayden M. J., Nguyen T. M., Whatman A., McMichael G. L., Chalmers K. J. (2008). Application of multiplex-ready PCR for fluorescence-based SSR genotyping in barley and wheat. Molecular Breeding, 21: 271-281.

Kosambi D. D. (1944). The estimation of map distances from recombination values. Annals Eugenics, 12: 172-175.

Lucchin M., Varotto S., Barcaccia G. and Parrini P. (2008). Chicory and Endive. In: Handbook of Plant Breeding, Vegetables I: Asteraceae, Brassicaceae, Chenopodicaceae. Edited by Jaime Prohens-Tomás and Fernando Nuez. Springer Science, New York, USA. pp. 1-46.

Mariani C., De Beuckeleer M., Trueltner J., Leemans J. and Goldberg R. B. (1990). Induction of male sterility in plants by a chimaeric ribonuclease gene. Nature, 347: 737-741.

Monegér F. and Smart C. J. (1994). Nuclear restoration of cytoplasmic male sterility in sunflower is associated with the tissue-specific regulation of a novel mitochondrial gene. EMBO J., 13(1): 8-17.

Rambaud C., Dubois J. and Vasseur J. (1993). Male-sterile chicory cybrids obtained by intergeneric protoplast fusion. Theoretical Applied Genetics, 87: 347-352.

Rambaud C., Bellamy A. Dubreucq A., Bourquin J-C. and Vasseur J. (1997). Molecular analysis of the fourth progeny of plants derived from cytoplasmic male sterile chicory cybrid. Plant Breeding, 116: 481-486.

Dubreucq A., Berthe B., Asset J. F., Boulidard L., Budar F., Vasseur J. and Rambaud C. (1999). Analyses of mitochondrial DNA structure and expression in three cytoplasmic male-sterile chicories originating from somatic hybridisation between fertile chicory and CMS sunflower protoplasts. Theoretical Applied Genetics 99, 1094-1105.

Reynaerts A., Van de Wiele H., de Sutter G. and Janssens J. (1993). Engineered genes for fertility control and their application in hybrid seed production. Scientia Horticulturae, 55: 125-139.

Stam P. and Van Ooijen J. W. (1995). JOINMAP™ version 2.0: Software for the calculation of genetic linkage maps. CPRO-DLO, Wageningen, The Netherlands.

Varotto S., Nenz E., Lucchin M. and Parrini P. (2001). Production of asymmetric somatic hybrid plants between *Cichorium intybus* and *Helianthus annuus*. Theoretical Applied Genetics, 102: 950-956.

Vos P., Hogers R., Bleeker M., Reijans M., Van de Lee T., Homes M., Frijters A., Pot J., Peleman J., Kuiper M. and Zabeau M. (1995). AFLP: A new technique for DNA fingerprinting. Nucleic Acids Research, 23: 4407-4414.

The invention claimed is:

1. F1 hybrid leaf chicory plants or parts or derivatives thereof,
   wherein the F1 hybrid plants or parts or derivatives thereof are each heterozygous for a recessive (ms) allele for which a male sterile leaf chicory plant is homozygous, and wherein said F1 hybrid is produced by crossing said male sterile leaf chicory plant with a male fertile leaf chicory plant, wherein the male sterile leaf chicory plant comprises a male sterile mutant of *Cichorium intybus* subsp. *intybus* var. *foliosum* leaf chicory plants or parts thereof, wherein the male sterile mutant and parts thereof:
   1) shows a cytological phenotype characterized by shapeless, small and shrunken microspores in dehiscent anthers as compared to wild-type leaf chicory plants, wherein said shrunken microspores arrest their development at the uninucleate stage, collapsing before their release from the tetrads; and
   2) wherein said male sterile mutant leaf chicory plants and parts and derivatives thereof each comprises a sterility trait which is controlled by a nuclear recessive mutation (ms) conferred by a single gene linked 5.8 cM apart to a polymorphic molecular marker locus finely mapped on linkage group 4, said molecular marker locus comprising a microsatellite or simple sequence repeat (TC)n target DNA region comprising a variable number (n) of thymine-cytosine (TC) repeats in SEQ ID NOs: 1 or 2, wherein the male sterile leaf chicory plants are homozygous for the recessive (ms) allele;
   wherein said male sterile mutant is selected by genotyping the leaf chicory plants or parts or derivatives thereof by analysing their DNA for the simple sequence repeat (TC)n in SEQ ID NO:1 or SEQ ID NO:2, and comparing genotypes of leaf chicory plants to a male sterile genotype of reference (msms) for the (TC)n target DNA region, said male sterile mutant being selected due to having both marker alleles comprising said simple sequence repeat (TC)n in SEQ ID NOs: 1 or 2; where n of (TC)n is 27 or 28.

2. Progeny leaf chicory plants or parts or derivatives thereof, said progeny plants obtained by at least one of crossing the F1 hybrid plants of claim 1 with each other, or by selfing the F1 hybrid plants of claim 1,
   wherein said progeny leaf chicory plants or parts or derivatives thereof are each heterozygous for the nuclear recessive (ms) allele.

3. F1 hybrid leaf chicory plants or parts or derivatives thereof,
   wherein the F1 hybrid plants or parts or derivatives thereof are each heterozygous at a locus for a single nuclear gene that controls male sterility (Msms), and wherein said F1 hybrid is produced by crossing a male sterile leaf chicory plant homozygous for the recessive mutant allele (ms), with a male fertile leaf chicory plant homozygous for the dominant wild type allele (Ms),
   wherein the male sterile leaf chicory plant comprises a male sterile mutant of *Cichorium intybus* subsp. *intybus* var. *foliosum* leaf chicory plants or parts thereof, wherein the genotype responsible for male sterility in the male sterile mutant and parts thereof is homozygous for the recessive mutant allele (ms) of the single nuclear gene, said nuclear gene linked 5.8 cM apart to a polymorphic molecular marker, said marker comprising SEQ ID NOS:1 or 2, wherein said marker and the recessive mutant allele (ms) are located on linkage group 4 of the *Cichorium intybus* genome consensus map,
   wherein the male sterile leaf chicory plants homozygous for said recessive mutant (ms) allele also have both alleles of said marker comprising a single sequence repeat (TC)n in SEQ ID NOs: 1 or 2, wherein n of said (TC)n is 27 or 28.

* * * * *

SEQUENCE LISTING

```
<160> NUMBER OF SEQ ID NOS: 13

<210> SEQ ID NO 1
<211> LENGTH: 42
<212> TYPE: DNA
<213> ORGANISM: Cichorium sp.

<400> SEQUENCE: 1
tgagtgattc tcggagagtt tccagagatc attgcttgtg ta                          42

<210> SEQ ID NO 2
<211> LENGTH: 99
<212> TYPE: DNA
<213> ORGANISM: Cichorium sp.

<400> SEQUENCE: 2
cttggaggtg tgagtgattc tcggagagtt tccagagatc attgcttgtg taattctcgc        60
tgatttcagt tcattgtcgt ctctctttgc tgtttcgta                               99

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```
cttggaggtg tgagtgattc t                                                 21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tacgaaacag caaagagaga c                                                 21

<210> SEQ ID NO 5
<211> LENGTH: 178
<212> TYPE: DNA
<213> ORGANISM: Cichorium intybus

<400> SEQUENCE: 5
gccattcctt tcaagagcag atcttaaaag tctaaagggt tgtgaattg tgtgtgtgcg        60 tgtgtgtgtg tgtaaattat tatggtccta aaatggatga tatttgtatt taagatctcc     120
atgcttgttt atcaactctc ttctatgata tgaacaaata ttgttgcggt tttgggtt       178

<210> SEQ ID NO 6
<211> LENGTH: 163
<212> TYPE: DNA
<213> ORGANISM: Cichorium sp.
<220> FEATURE:
<221> NAME/KEY: misc_feature
<222> LOCATION: (31)..(96)
<223> OTHER INFORMATION: This region may encompass 27 to 33 "tc"
      repeating units

<400> SEQUENCE: 6
cttggaggtg tgagtgattc tcggagagtt tctctctctc tctctctctc tctctctctc       60
tctctctctc tctctctctc tctctctctc tctccaga gatcattgct tgtgtaattc        120
tcgctgattt cagttcattg tcgtctctct ttgctgtttc gta                        163

<210> SEQ ID NO 7
<211> LENGTH: 66
<212> TYPE: DNA
<213> ORGANISM: Cichorium sp.
<220> FEATURE:
<221> NAME/KEY: misc_feature
<222> LOCATION: (1)..(66)
<223> OTHER INFORMATION: This sequence may encompass 27 to 33 "tc"
      repeating units

<400> SEQUENCE: 7
tctctctctc tctctctctc tctctctctc tctctctctc tctctctctc tctctctctc       60
tctctc                                                                  66

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(20)
<223> OTHER INFORMATION: This region may encompass 1 to 10 "tg"
      repeating units -continued

```
<220> FEATURE:
<221> NAME/KEY: misc_feature
<222> LOCATION: (23)..(42)
<223> OTHER INFORMATION: This region may encompass 1 to 10 "tg"
      repeating units
<220> FEATURE:
<223> OTHER INFORMATION: See specification as filed for detailed
      description of substitutions and preferred embodiments

<400> SEQUENCE: 8
tgtgtgtgtg tgtgtgtgtg cgtgtgtgtg tgtgtgtgtg tg                    42

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttgtaaaacg acggccagt                                              19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccattcctt tcaagagcag                                             20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aacccaaaac cgcaacaata                                             20

<210> SEQ ID NO 12
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(56)
<223> OTHER INFORMATION: This sequence may encompass 27 to 28 "tc"
      repeating units

<400> SEQUENCE: 12
tctctctctc tctctctctc tctctctctc tctctctctc tctctctctc tctctc    56

<210> SEQ ID NO 13
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (1)..(78)
<223> OTHER INFORMATION: This sequence may encompass 25 to 39 "tc"
      repeating units

<400> SEQUENCE: 13
tctctctctc tctctctctc tctctctctc tctctctctc tctctctctc tctctctctc        60
tctctctctc tctctctc                                                      78
```